United States Patent
Moon et al.

(10) Patent No.: US 11,987,552 B2
(45) Date of Patent: May 21, 2024

(54) POLYMERIC PHENOLIC ANTIOXIDANTS

(71) Applicant: Milliken & Company, Spartanburg, SC (US)

(72) Inventors: Nicholas G. Moon, Greer, SC (US); Haihu Qin, Greer, SC (US); Sharon A. Free, Chesnee, SC (US); Mark E. Ragsdale, Duncan, SC (US); Michael Hong, Greer, SC (US)

(73) Assignee: Milliken & Company, Spartanburg, SC (US)

( * ) Notice: Subject to any disclaimer, the term of this patent is extended or adjusted under 35 U.S.C. 154(b) by 547 days.

(21) Appl. No.: 16/523,523

(22) Filed: Jul. 26, 2019

(65) Prior Publication Data
US 2020/0031756 A1 Jan. 30, 2020

Related U.S. Application Data

(60) Provisional application No. 62/711,458, filed on Jul. 27, 2018.

(51) Int. Cl.
| | |
|---|---|
| *C07C 69/675* | (2006.01) |
| *C08G 18/16* | (2006.01) |
| *C08G 18/24* | (2006.01) |
| *C08G 18/28* | (2006.01) |
| *C08G 18/32* | (2006.01) |
| *C08G 18/48* | (2006.01) |
| *C08G 18/76* | (2006.01) |
| *C08K 5/00* | (2006.01) |

(52) U.S. Cl.
CPC .......... *C07C 69/675* (2013.01); *C08G 18/165* (2013.01); *C08G 18/244* (2013.01); *C08G 18/284* (2013.01); *C08G 18/3203* (2013.01); *C08G 18/48* (2013.01); *C08G 18/7621* (2013.01); *C08K 5/005* (2013.01); *C07C 2601/16* (2017.05); *C08G 2110/0008* (2021.01); *C08G 2110/0083* (2021.01); *C08G 2290/00* (2013.01)

(58) Field of Classification Search
CPC . C07C 69/675; C07C 2601/16; C08G 18/284; C08G 18/3203; C08G 18/7621; C08G 2110/0008; C08G 2110/0083; C08G 18/165; C08G 18/244; C08G 2290/00; C08G 18/48; C08K 5/005
See application file for complete search history.

(56) References Cited

U.S. PATENT DOCUMENTS

| | | |
|---|---|---|
| 3,957,920 A | 5/1976 | Kleiner et al. |
| 4,032,562 A | 6/1977 | Dexter et al. |
| 4,078,091 A | 3/1978 | Dale et al. |
| 4,098,709 A | 7/1978 | Hanauer et al. |
| 4,107,144 A * | 8/1978 | Russell ................. C08F 110/00 526/348 |
| 4,430,235 A | 2/1984 | Chu et al. |
| 7,169,844 B2 | 1/2007 | Inokami |
| 7,323,511 B2 | 1/2008 | Cholli et al. |
| 2006/0189727 A1* | 8/2006 | Kreitschmann ...... C08G 18/664 524/334 |
| 2007/0106059 A1 | 5/2007 | Cholli et al. |
| 2010/0084607 A1 | 4/2010 | Cholli et al. |
| 2016/0264757 A1 | 9/2016 | Krebs et al. |

FOREIGN PATENT DOCUMENTS

| | | | | |
|---|---|---|---|---|
| DE | 19710081 A1 * | 9/1998 | ........... | C08G 64/186 |
| EP | 0 463 835 A2 | 1/1992 | | |
| EP | 0 674 614 A1 | 10/1995 | | |
| EP | 1 654 313 A1 | 5/2006 | | |
| JP | S60-127318 A | 7/1985 | | |
| JP | 7-242840 A * | 9/1995 | | |
| WO | WO 03/051816 A1 | 6/2003 | | |
| WO | WO-2017207611 A1 * | 12/2017 | ............. | B32B 17/04 |
| WO | WO-2018114901 A1 * | 6/2018 | ........... | C08G 64/186 |

OTHER PUBLICATIONS

PCT/US2019/043681 International Search Report, filed Jul. 26, 2019, 5 pages.
PCT/US2019/043681 Written Opinion of the International Searching Authority, filed Jul. 26, 2019, 13 pages.

\* cited by examiner

*Primary Examiner* — Rabon A Sergent
(74) *Attorney, Agent, or Firm* — Robert M. Lanning

(57) ABSTRACT

A phenol compound comprises a phenyl group, a hydroxy group directly bonded to the phenyl group, and at least one polymeric substituent bound to the phenyl group. The polymeric substituent comprises three or more monomers units. A method for producing a polyurethane polymer comprises the steps of (a) providing a polyol; (b) providing a polyisocyanate compound; (c) providing the phenol compound described above; (d) combining the polyol, the polyisocyanate compound, and the phenol compound to produce a reaction mixture; and (e) allowing the polyol and the polyisocyanate compound to react to produce a polyurethane polymer.

17 Claims, No Drawings

US 11,987,552 B2

POLYMERIC PHENOLIC ANTIOXIDANTS

CROSS-REFERENCE TO RELATED APPLICATIONS

This application claims, pursuant to 35 U.S.C. § 119(e), priority to and the benefit of the filing date of U.S. Patent Application No. 62/711,458, which was filed on Jul. 27, 2018, the contents of which are hereby incorporated by reference.

TECHNICAL FIELD OF THE INVENTION

This application relates to phenol compounds that exhibit antioxidant properties and the use of the same as stabilizers or antioxidants for organic materials. More specifically, the application describes hindered phenol compounds comprising one or more polymeric substituents.

BACKGROUND

Antioxidants are a class of compounds used to stabilize materials (e.g., polymers) that are susceptible to oxidative degradation. One potential pathway to such oxidative degradation is through the formation of free radicals in the material. These free radicals can form through hydrogen abstraction or homolytic cleavage of carbon-carbon bonds when the material is exposed to heat, oxygen, ozone, or radiation (e.g., ultraviolet light). There are two main classes of antioxidants that are used to scavenge such free radicals and thereby stabilize the material. The first of these classes is sterically hindered phenol antioxidants. This class of antioxidants enjoys widespread use due to their effectiveness in scavenging radicals and their tendency not to discolor the materials to which they are added. The second of these classes of antioxidants is aromatic amines. Certain antioxidants are known to discolor the materials to which they are added. Further, when antioxidants are used in laundry care products, this tendency to discolor over time poses even greater problem. In particular, known antioxidants tend to be hydrophobic materials, which means that the materials will deposit onto certain fabric surfaces during laundering. Then, as the deposited antioxidants are themselves oxidized over time, they discolor and impart a dingy appearance to the fabric substrate. Thus, the use of known antioxidants is generally limited and fraught with trade-offs between antioxidant performance and deleterious side effects in the material to which they are added. Furthermore, antioxidants can migrate out of materials over time, posing environmental and other hazards. This tendency to migrate has become more of a concern as regulatory agencies have passed tighter regulations around the migration of additives. In response, some have advocated reducing antioxidants levels in the materials, but such reductions will leave the material susceptible to oxidative degradation and shorten its life.

Thus, a need remains for compounds that exhibit highly effective antioxidant properties, low deposition onto fabric surfaces, and low migration. The compounds described herein are believed to meet this need.

BRIEF SUMMARY OF THE INVENTION

In a first embodiment, the invention provides a phenol compound comprising a phenyl group, a hydroxy group directly bonded to the phenyl group, and at least one polymeric substituent bound to the phenyl group, the polymeric substituent comprising three or more monomers units.

In a second embodiment, the invention provides a method for producing a polyurethane polymer, the method comprising the steps of:
(a) providing a polyol;
(b) providing a polyisocyanate compound;
(c) providing a phenol compound comprising a phenyl group, a hydroxy group directly bonded to the phenyl group, and at least one polymeric substituent bound to the phenyl group, the polymeric substituent comprising three or more monomers units;
(d) combining the polyol, the polyisocyanate compound, and the phenol compound to produce a reaction mixture; and
(e) allowing the polyol and the polyisocyanate compound to react to produce a polyurethane polymer.

DETAILED DESCRIPTION OF THE INVENTION

The following definitions are provided to define several of the terms used throughout this application.

As used herein, the term "substituted alkyl groups" refers to univalent functional groups derived from substituted alkanes by removal of a hydrogen atom from a carbon atom of the alkane. In this definition, the term "substituted alkanes" refers to compounds derived from acyclic unbranched and branched hydrocarbons in which (1) one or more of the hydrogen atoms of the hydrocarbon is replaced with a non-hydrogen atom (e.g., a halogen atom) or a non-alkyl functional group (e.g., hydroxy group, aryl group, heteroaryl group) and/or (2) the carbon-carbon chain of the hydrocarbon is interrupted by an oxygen atom (as in an ether), a nitrogen atom (as in an amine), or a sulfur atom (as in a sulfide).

As used herein, the term "substituted cycloalkyl groups" refers to univalent functional groups derived from substituted cycloalkanes by removal of a hydrogen atom from a carbon atom of the cycloalkane. In this definition, the term "substituted cycloalkanes" refers to compounds derived from saturated monocyclic and polycyclic hydrocarbons (with or without side chains) in which (1) one or more of the hydrogen atoms of the hydrocarbon is replaced with a non-hydrogen atom (e.g., a halogen atom) or a non-alkyl functional group (e.g., hydroxy group, aryl group, heteroaryl group) and/or (2) the carbon-carbon chain of the hydrocarbon is interrupted by an oxygen atom, a nitrogen atom, or a sulfur atom.

As used herein, the term "substituted aryl groups" refers to univalent functional groups derived from substituted arenes by removal of a hydrogen atom from a ring carbon atom. In this definition, the term "substituted arenes" refers to compounds derived from monocyclic and polycyclic aromatic hydrocarbons in which one or more of the hydrogen atoms of the hydrocarbon is replaced with a non-hydrogen atom (e.g., a halogen atom) or a functional group (e.g., a hydroxy group, a carboxyl group, an alkyl group, a heteroaryl group).

As used herein, the term "substituted alkoxy groups" refers to univalent functional groups having the general formula R'—O—, where R' is a substituted alkyl group.

As used herein, the term "substituted aryloxy groups" refers to univalent functional groups having the general formula R"—O—, wherein R" is a substituted aryl group.

In a first embodiment, the invention provides a phenol compound. The phenol compound comprises a phenyl group and a hydroxy group directly bonded to the phenyl group (i.e., the hydroxy group replaces a hydrogen atom of the phenyl group such that the oxygen atom of the hydroxy group is directly bonded to a carbon atom of the phenyl group). The phenol compound further comprises at least one polymeric substituent bound thereto. As used herein, the term "polymeric substituent" refers to a substituent comprising three or more monomer units. In such polymeric substituent, the monomer units can be the same or different. Further, at least two of the monomer units preferably are connected in series. For example, the polymeric substituent can be bound to a nitrogen linking group, with the monomer units being distributed among one or two of the valences of the nitrogen linking group (the third valence providing a link to the aromatic group). Preferably, the polymeric substituent comprises three or more monomer units connected in series.

The polymeric substituent can comprise any suitable monomer unit or combination of different monomer units. In a preferred embodiment, the polymeric substituent comprises monomer units independently selected from the group consisting of alkyleneoxy groups, oxoalkyleneoxy groups, oxoalkyleneamine groups, alkyleneamine groups, substituted alkylene groups, saccharide groups, halomethylalkyleneoxy groups, and quaternaryammoniummethylalkyleneoxy groups. In another preferred embodiment, the polymeric substituent comprises monomer units independently selected from the group consisting of alkyleneoxy groups and oxoalkyleneoxy groups. Preferably, the polymeric substituent comprises monomer units independently selected from the group consisting of ethyleneoxy, propyleneoxy, and butyleneoxy. The polymeric substituent can be terminated with any suitable terminal group. For example, the polymeric substituent can be terminated with another phenol moiety. Thus, in such an embodiment, the phenol compound would be a dimer in which two phenol moieties are linked by an intervening polymeric substituent. In such an embodiment, these phenol moieties can be the same or they can be different. In a preferred embodiment, the phenol moieties are the same. Preferably, the polymeric substituent is terminated with a terminal group comprising an active hydrogen atom. As used herein, the term "active hydrogen" refers to a hydrogen atom that is bonded to an atom that is more electronegative than carbon. Suitable active hydrogen-containing groups include, but are not limited to, a hydroxy group, amine groups, amide groups, and sulfhydryl groups (e.g., thiols). Preferably, the polymeric substituent terminates in a hydroxy group.

Suitable alkyleneoxy groups include those of Formula (C) below:

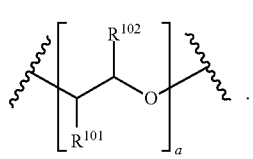
(C)

In the structure of Formula (C) and those that follow, the bonds truncated by wavy lines represent bonds to adjacent portions of the phenol compound, such as the aromatic groups described above and the terminal group of the polymeric substituent. In the structure of Formula (C), each $R^{101}$ and $R^{102}$ group is independently selected from the group consisting of hydrogen, alkyl, aryl, alkoxyalkyl, and aryloxyalkyl. Preferably, each $R^{101}$ and $R^{102}$ group is independently selected from the group consisting of hydrogen and alkyl (e.g., $C_1$-$C_4$ alkyl). The variable a is an integer equal to or greater than 1 (e.g., from 1 to about 100). For each monomer unit in the alkyleneoxy group, the $R^{101}$ and $R^{102}$ groups are independently selected from the recited group. Thus, when the variable a is greater than 1, the alkyleneoxy group can be comprised of two or more monomer units covalently bonded to form the alkyleneoxy group. When the alkyleneoxy group comprises two or more monomer units, these monomer units can be arranged in either a block configuration or in a random configuration, but a block configuration generally is more preferred. As noted above, in a preferred embodiment, the alkyleneoxy group comprises monomer units independently selected from the group consisting of ethyleneoxy, propyleneoxy, and butyleneoxy. A suitable example of such an alkyleneoxy group is Formula (CI) below:

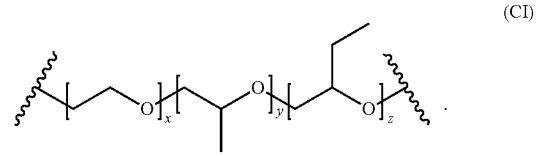
(CI)

In the structure of Formula (CI), the variables x, y, and z are independently selected from the group consisting of zero and positive integers (e.g., positive integers from 1 to about 100). Preferably, the sum of x, y, and z is 2 or more or 3 or more (e.g., 2 to about 300, 3 to about 300, 2 to about 200, 3 to about 200, 2 to about 100, 3 to about 100, 2 to about 50, 3 to about 50, 2 to about 30, 3 to about 30, 2 to about 25, 3 to about 25, 2 to about 20, 3 to about 20, 2 to about 15, 3 to about 15, 2 to about 10, or 3 to about 10). In certain possibly preferred embodiments, the alkyleneoxy group comprises ethyleneoxy and propyleneoxy monomer units arranged in a block configuration. Suitable examples of such alkyleneoxy groups include those of Formulae (CII) and (CIII) below

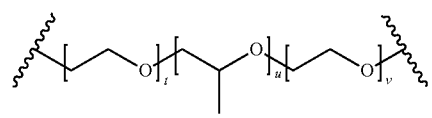
(CII)

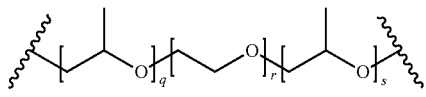
(CIII)

In the structures of Formulae (CII) and (CIII), the variables, t, u, v, q, r, and s are independently selected from the group consisting of zero and positive integers (e.g., positive integers from 1 to about 100). Preferably, the sum of t, u, and v and q, r, and s is 2 or more or 3 or more (e.g., 2 to about 300, 3 to about 300, 2 to about 200, 3 to about 200, 2 to about 100, 3 to about 100, 2 to about 50, 3 to about 50, 2 to about 30, 3 to about 30, 2 to about 25, 3 to about 25, 2 to about 20, 3 to about 20, 2 to about 15, 3 to about 15, 2 to about 10, or 3 to about 10).

Suitable oxoalkyleneoxy groups include those of Formula (CX) below:

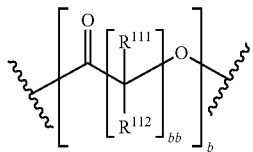
(CX)

In the structure of Formula (CX), each $R^{111}$ and $R^{112}$ group is independently selected from the group consisting of hydrogen, hydroxy, and alkyl. Preferably, each $R^{111}$ and $R^{112}$ group is independently selected from the group consisting of hydrogen and alkyl (e.g., $C_1$-$C_{10}$ alkyl or $C_1$-$C_4$ alkyl). The variable b is an integer equal to or greater than 1 (e.g., from 1 to about 100), more preferably 2 to about 100 or 3 to about 100 (e.g., 2 to about 300, 3 to about 300, 2 to about 200, 3 to about 200, 2 to about 100, 3 to about 100, 2 to about 50, 3 to about 50, 2 to about 30, 3 to about 30, 2 to about 25, 3 to about 25, 2 to about 20, 3 to about 20, 2 to about 15, 3 to about 15, 2 to about 10, or 3 to about 10). The variable bb is an integer from 1 to 12, more preferably 1-5. For each monomer unit in the oxoalkyleneoxy group, the $R^{111}$ and $R^{112}$ groups are independently selected from the recited group. Thus, when the variable b is greater than 1, the oxoalkyleneoxy group can be comprised of two or more monomer units covalently bonded to form the oxoalkyleneoxy group. When the oxoalkyleneoxy group comprises two or more monomer units, these monomer units can be arranged in either a block configuration or in a random configuration, but a block configuration generally is more preferred.

Suitable oxoalkyleneamine groups include those of Formula (CX) below:

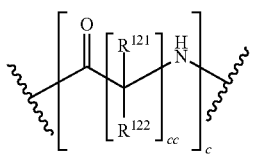
(CXX)

In the structure of Formula (CXX), each $R^{121}$ and $R^{122}$ group is independently selected from the group consisting of hydrogen, hydroxy, and alkyl. Preferably, each $R^{121}$ and $R^{122}$ group is independently selected from the group consisting of hydrogen and alkyl (e.g., $C_1$-$C_{10}$ alkyl or $C_1$-$C_4$ alkyl). The variable c is an integer equal to or greater than 1 (e.g., from 1 to about 100), more preferably 2 to about 100 or 3 to about 100 (e.g., 2 to about 300, 3 to about 300, 2 to about 200, 3 to about 200, 2 to about 100, 3 to about 100, 2 to about 50, 3 to about 50, 2 to about 30, 3 to about 30, 2 to about 25, 3 to about 25, 2 to about 20, 3 to about 20, 2 to about 15, 3 to about 15, 2 to about 10, or 3 to about 10). The variable cc is an integer from 1 to 12, more preferably 1-5. For each monomer unit in the oxoalkyleneamine group, the $R^{121}$ and $R^{122}$ groups are independently selected from the recited group. Thus, when the variable c is greater than 1, the oxoalkyleneamine group can be comprised of two or more monomer units covalently bonded to form the oxoalkyleneamine group. When the oxoalkyleneamine group comprises two or more monomer units, these monomer units can be arranged in either a block configuration or in a random configuration, but a block configuration generally is more preferred.

Suitable alkyleneamine groups include those of Formula (CXX) below:

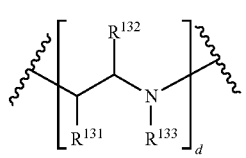
(CXX)

In the structure of Formula (CXX), each $R^{131}$ and $R^{132}$ group is independently selected from the group consisting of hydrogen and alkyl (e.g., $C_1$-$C_{10}$ alkyl or $C_1$-$C_4$ alkyl), and each $R^{133}$ is selected from the group consisting of hydrogen and alkylamine groups. The variable d is an integer equal to or greater than 1 (e.g., 1 to about 100), more preferably 2 to about 100 or 3 to about 100 (e.g., 2 to about 300, 3 to about 300, 2 to about 200, 3 to about 200, 2 to about 100, 3 to about 100, 2 to about 50, 3 to about 50, 2 to about 30, 3 to about 30, 2 to about 25, 3 to about 25, 2 to about 20, 3 to about 20, 2 to about 15, 3 to about 15, 2 to about 10, or 3 to about 10). For each monomer unit in the alkyleneamine group, the $R^{131}$, $R^{132}$, $R^{133}$ groups are independently selected from the recited group. Thus, when the variable d is greater than 1, the alkyleneamine group can be comprised of two or more monomer units covalently bonded to form the alkyleneamine group. Further, when the variable d is greater than 2, the monomer units can be arranged in either a linear or a branched configuration. When the alkyleneamine group comprises two or more monomer units, these monomer units can be arranged in either a block configuration or in a random configuration, but a block configuration generally is more preferred.

Suitable substituted alkylene groups include those of Formula (CXXX) below:

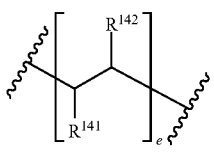
(CXXX)

In the structure of Formula (CXXX), each $R^{141}$ and $R^{142}$ group is independently selected from the group consisting of hydrogen, hydroxy, alkyl (e.g., $C_1$-$C_{10}$ alkyl or $C_1$-$C_4$ alkyl), —$OR^{143}$ where $R^{143}$ is acyl (e.g., $C_2$-$C_{20}$ acyl, $C_2$-$C_{10}$ acyl, or $C_2$-$C_4$ acyl), and —$C(O)OR^{144}$ where $R^{144}$ is hydrogen or alkyl (e.g., $C_1$-$C_{10}$ alkyl or $C_1$-$C_4$ alkyl), provided one of $R^{141}$ and $R^{142}$ is hydroxy, —$OR^{143}$, or —$C(O)OR^{144}$. In a preferred embodiment, each $R^{141}$ and $R^{142}$ group is selected from the group consisting of hydrogen and hydroxy. In another preferred embodiment, one of $R^{141}$ and $R^{142}$ is hydrogen and the other is —$OR^{143}$, with $R^{143}$ preferably being $C_2$-$C_4$ acyl (e.g., acetyl). The variable e is an integer equal to or greater than 1 (e.g., 1 to about 100), more preferably 2 to about 100 or 3 to about 100 (e.g., 2 to about 300, 3 to about 300, 2 to about 200, 3 to about 200, 2 to about 100, 3 to about 100, 2 to about 50, 3 to about 50, 2 to about 30, 3 to about 30, 2 to about 25, 3 to about 25, 2 to about 20, 3 to about 20, 2 to about 15, 3 to about 15, 2 to about 10, or 3 to about 10). For each monomer unit in the substituted alkylene group, the $R^{141}$ and $R^{142}$ groups are independently selected from the recited group. Thus, when the variable e is greater than 1, the substituted alkylene group can be comprised of two or more monomer units covalently bonded to form the substituted alkylene group. When the substituted alkylene group comprises two or more monomer units, these monomer units can be arranged in either a block configuration or in a random configuration, but a block configuration generally is more preferred.

Suitable saccharide groups include those of Formula (CL) below:

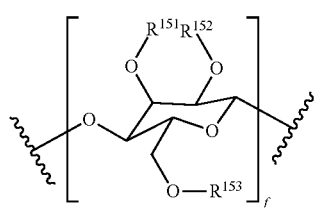

(CL)

In the structure of Formula (CL), each $R^{151}$, $R^{152}$, and $R^{153}$ group is independently selected from the group consisting of hydrogen and —CH$_2$CO$_2$H. The variable f is an integer equal to or greater than 1 (e.g., from 1 to about 100), more preferably 2 to about 100 or 3 to about 100 (e.g., 2 to about 300, 3 to about 300, 2 to about 200, 3 to about 200, 2 to about 100, 3 to about 100, 2 to about 50, 3 to about 50, 2 to about 30, 3 to about 30, 2 to about 25, 3 to about 25, 2 to about 20, 3 to about 20, 2 to about 15, 3 to about 15, 2 to about 10, or 3 to about 10). For each monomer unit in the saccharide group, the $R^{151}$, $R^{152}$, and $R^{153}$ groups are independently selected from the recited group. Thus, when the variable f is greater than 1, the saccharide group can be comprised of two or more monomer units covalently bonded to form the saccharide group. When the saccharide group comprises two or more monomer units, these monomer units can be arranged in either a block configuration or in a random configuration, but a block configuration generally is more preferred.

Suitable halomethylalkyleneoxy groups include those of Formula (CLX) below:

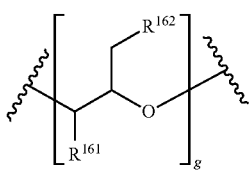

(CLX)

In the structure of Formula (CLX), each $R^{161}$ is independently selected from the group consisting of hydrogen and alkyl (e.g., $C_1$-$C_{10}$ alkyl or $C_1$-$C_4$ alkyl), and each $R^{162}$ is an independently selected halogen (e.g., chlorine). The variable g is an integer equal to or greater than 1 (e.g., from 1 to about 100), more preferably 2 to about 100 or 3 to about 100 (e.g., 2 to about 300, 3 to about 300, 2 to about 200, 3 to about 200, 2 to about 100, 3 to about 100, 2 to about 50, 3 to about 50, 2 to about 30, 3 to about 30, 2 to about 25, 3 to about 25, 2 to about 20, 3 to about 20, 2 to about 15, 3 to about 15, 2 to about 10, or 3 to about 10). For each monomer unit in the halomethylalkyleneoxy group, the $R^{161}$ and $R^{162}$ groups are independently selected from the recited groups. Thus, when the variable g is greater than 1, the halomethylalkyleneoxy group can be comprised of two or more monomer units covalently bonded to form the halomethylalkyleneoxy group. When the halomethylalkyleneoxy group comprises two or more monomer units, these monomer units can be arranged in either a block configuration or in a random configuration, but a block configuration generally is more preferred.

Suitable quaternaryammoniummethylalkyleneoxy groups include those of Formula (CLXX) below:

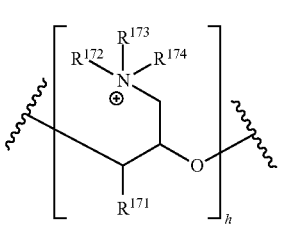

(CLXX)

In the structure of Formula (CLXX), each $R^{171}$ is independently selected from the group consisting of hydrogen and alkyl (e.g., $C_1$-$C_{10}$ alkyl or $C_1$-$C_4$ alkyl), and each $R^{172}$, $R^{173}$, $R^{174}$ is independently selected from the group consisting of alkyl and hydroxyalkyl (e.g., $C_1$-$C_{10}$ hydroxyalkyl or $C_1$-$C_4$ hydroxyalkyl). The variable h is an integer equal to or greater than 1 (e.g., from 1 to about 100), more preferably 2 to about 100 or 3 to about 100 (e.g., 2 to about 300, 3 to about 300, 2 to about 200, 3 to about 200, 2 to about 100, 3 to about 100, 2 to about 50, 3 to about 50, 2 to about 30, 3 to about 30, 2 to about 25, 3 to about 25, 2 to about 20, 3 to about 20, 2 to about 15, 3 to about 15, 2 to about 10, or 3 to about 10). For each monomer unit in the quaternaryammoniummethylalkyleneoxy group, the $R^{171}$, $R^{172}$, $R^{173}$, and $R^{174}$ groups are independently selected from the recited groups. Thus, when the variable h is greater than 1, the quaternaryammoniummethylalkyleneoxy group can be comprised of two or more monomer units covalently bonded to form the quaternaryammoniummethylalkyleneoxy group. When the quaternaryammoniummethylalkyleneoxy group comprises two or more monomer units, these monomer units can be arranged in either a block configuration or in a random configuration, but a block configuration generally is more preferred.

The polymeric substituent can comprise two or more of such groups (i.e., alkyleneoxy groups, oxoalkyleneoxy groups, oxoalkyleneamine groups, alkyleneamine groups, substituted alkylene groups, saccharide groups, halomethylalkyleneoxy groups, and quaternaryammoniummethylalkyleneoxy groups) covalently bonded together. For example, the polymeric substituent can comprise an alkyleneoxy group of Formula (C) covalently bonded to an oxoalkyleneoxy group of Formula (CX).

The polymeric substituent can be directly bonded to the phenyl group, or the polymeric substituent can be bonded to an intervening functional group or atom that links the polymeric substituent and the phenyl group. These intervening functional groups or atoms ("linking groups") can be any suitable group. When the polymeric substituent is bonded to the phenyl group through a linking group, the linking group preferably is directly bonded to a carbon atom of the phenyl group. Preferably, the linking group is selected from the group consisting of an oxygen atom, a sulfur atom, a secondary amine group, a tertiary amine group, an alkoxy group, an ester group, an amide group, an alkylamine group (bearing either a secondary or tertiary amine group), and a carbamate group. A secondary amine linking group is one in which the linking group's amine nitrogen is bonded to a hydrogen atom, the phenyl group, and the polymeric substituent. A tertiary amine linking group is one in which the linking group's amine nitrogen is bonded to the phenyl group, the polymeric substituent, and a non-hydrogen group. For such tertiary amine linking groups, the non-hydrogen group can be any suitable organic group, such as an alkyl group or another polymeric substituent as described herein. In a preferred embodiment, the linking group is an oxygen atom directly bonded to the polymeric substituent and the phenyl group. In another preferred embodiment, the linking group is an ester group or an amide group directly bonded to the polymeric substituent and the phenyl group.

The polymeric substituent can be bonded (either directly or through a suitable linking group) to any suitable position on the phenyl group. For example, the polymeric substituents can be disposed at the meta or para position relative to the hydroxy group. Preferably, the hydroxy group and the polymeric substituent (or the linking group that is bonded to the polymeric substituent) are disposed in the para position relative to each other on the phenyl group.

The remaining positions on the aryl group of the phenol compound (i.e., those positions not bonded to the hydroxy group or the polymer substituent(s)) can be unsubstituted or substituted with any suitable groups. In a preferred embodiment, the phenol compound comprises one or more steric hindering groups directly bonded to the phenyl group (i.e., the steric hindering group replaces a hydrogen atom of the phenyl group such that the oxygen atom of the hydroxy group is directly bonded to a carbon atom of the phenyl group). Preferably, the steric hindering group is bonded to the phenyl group in a position that is ortho to the hydroxy group. In a particularly preferred embodiment, the phenol compound comprises two steric hindering groups, each of which is bonded to the phenyl group in a position that is ortho to the hydroxy group.

As utilized herein, the term "steric hindering group" refers to any functional group that produces a steric effect by crowding the adjacent hydroxy group. In a preferred embodiment, the steric hindering group is selected from the group consisting of hydroxy groups, alkyl groups, substituted alkyl groups, cycloalkyl groups, substituted cycloalkyl groups, aryl groups, substituted aryl groups, heteroaryl groups, substituted heteroaryl groups, alkoxy groups, substituted alkoxy groups, aryloxy groups, and substituted aryloxy groups. Preferably, the steric hindering group is selected from the group consisting of hydroxy groups, alkyl groups, and substituted alkyl groups. More preferably, the steric hindering group is an alkyl group (e.g., $C_1$-$C_8$ alkyl group), with branched alkyl groups (e.g., $C_3$-$C_8$ branched alkyl groups) being more preferred. In a particularly preferred embodiment, the steric hindering group is a tert-butyl group.

In a preferred embodiment, the invention provides a phenol compound of Formula (I)

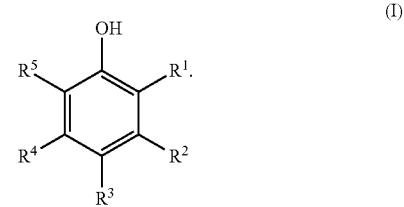

In the structure of Formula (I), $R^1$, $R^2$, $R^3$, $R^4$, and $R^5$ are independently selected from the group consisting of hydrogen, hydroxy groups, alkyl groups, substituted alkyl groups, cycloalkyl groups, substituted cycloalkyl groups, aryl groups, substituted aryl groups, heteroaryl groups, substituted heteroaryl groups, alkoxy groups, substituted alkoxy groups, aryloxy groups, substituted aryloxy groups, and $R^w$, provided at least one of $R^1$, $R^2$, $R^3$, $R^4$, and $R^5$ is $R^w$. $R^w$ is selected from the group consisting of —$(CH_2)_n$—O—$R^a$, —$(CH_2)_n$—C(O)O—$R^a$, —$(CH_2)_n$—$NR^aR^b$, —$(CH_2)_n$—C(O)—$NR^aR^b$, —$(CH_2)_n$—C(O)—N(H)—$(CH_2)_m$—$NR^aR^b$, —C(O)$R^a$, —C(O)O$R^a$, —C(O)$NR^aR^b$, —OC(O)$R^a$, —OC(O)O$R^a$, —OC(O)$NR^aR^b$, —S(O)$_2R^a$, —S(O)$_2OR^a$, —S(O)$_2NR^aR^b$, —$NR^aC(O)R^b$, —$NR^aC(O)OR^b$, —$NR^aC(O)SR^b$, —$NR^aC(O)NR^bR^c$, —P(O)$_2R^a$, —P(O)(O$R^a$)$_2$, —P(O)(O$R^a$)O⁻, where the variable n is an integer from 0 to 10 (preferably from 0 to 4, more preferably 0 to 2, and most preferably 2), the variable m is an integer from 1 to 10 (preferably 1 to 4, and most preferably 2-3), and at least one of $R^a$ and $R^b$ in the pendant group is a polymeric substituent as described above. More preferably, at least one of $R^a$ and $R^b$ in the group is —$R^yR^x$ or —$R^zR^yR^x$, where $R^x$ is selected from the group consisting of hydrogen and alkyl, $R^z$ is selected from the group consisting of alkoxy groups (e.g., $C_1$-$C_4$ alkoxy groups) and substituted alkoxy groups (e.g., $C_1$-$C_4$ substituted alkoxy groups), and $R^y$ is a polymeric substituent of Formula (C), (CX), (CXX), (CXXX), (CXL), (CL), (CLX), or (CLXX) or a polymeric substituent comprising two or more groups of Formula (C), (CX), (CXX), (CXXX), (CXL), (CL), (CLX), or (CLXX) covalently bonded together. Preferably, at least one of $R^1$, $R^2$, $R^3$, $R^4$, and $R^5$ (preferably $R^3$) is selected from the group consisting of —$(CH_2)_n$—O—$R^a$, —$(CH_2)_n$—C(O)O—$R^a$, —$(CH_2)_n$—$NR^aR^b$, and —$(CH_2)_n$—C(O)—$NR^aR^b$. In such embodiment, at least one of $R^a$ and $R^b$ in the pendant group is —$R^yR^x$ or —$R^zR^yR^x$, where $R^x$ is selected from the group consisting of hydrogen and alkyl (e.g., $C_1$-$C_{10}$ alkyl or $C_1$-$C_4$ alkyl) and $R^y$ is a polymeric substituent of Formula (C) or Formula (CX). Preferably, in such an embodiment, the variable n is 0-2 and $R^x$ is hydrogen or methyl, more preferably hydrogen. In a particularly preferred embodiment, $R^1$ and $R^5$ are independently selected alkyl groups (preferably $C_1$-$C_8$ alkyl groups, and more preferably tert-butyl groups), and $R^2$ and $R^4$ are hydrogen.

In a preferred embodiment of the structure of Formula (I), $R^1$ and $R^5$ are independently selected alkyl groups (preferably $C_1$-$C_8$ alkyl groups, and more preferably tert-butyl groups), $R^2$ and $R^4$ are hydrogen, $R^3$ is —$(CH_2)_n$—O—$R^a$, the variable n is an integer from 1 to 4 (preferably 1), $R^a$ is —$R^yR^x$, $R^x$ is selected from the group consisting of hydrogen and $C_1$-$C_4$ alkyl (preferably, $R^x$ is hydrogen), and $R^y$ is a polymeric substituent of Formula (CX).

In another preferred embodiment of the structure of Formula (I), $R^1$ and $R^5$ are hydroxy groups, $R^2$ and $R^4$ are hydrogen, $R^3$ is —$(CH_2)_n$—C(O)O—$R^a$, the variable n is an integer from 1 to 4 (preferably 0), $R^a$ is —$R^yR^x$, $R^x$ is selected from the group consisting of hydrogen and $C_1$-$C_4$ alkyl (preferably, $R^x$ is methyl), and $R^y$ is a polymeric substituent of Formula (C).

In yet another preferred embodiment of the structure of Formula (I), $R^1$ and $R^5$ are independently selected alkyl groups (preferably $C_1$-$C_8$ alkyl groups, and more preferably tert-butyl groups), $R^2$ and $R^4$ are hydrogen, $R^3$ is —$(CH_2)_n$—C(O)—N(H)—$(CH_2)_m$—$NR^aR^b$, the variable n is an integer from 1 to 4 (preferably 2), the variable m is an integer from 1 to 4 (preferably 3), $R^a$ and $R^b$ are independently selected —$R^yR^x$ groups, each $R^x$ is independently selected from the group consisting of hydrogen and $C_1$-$C_4$ alkyl (preferably, each $R^x$ is hydrogen), and each $R^y$ is a polymeric substituent of Formula (CX).

In a preferred embodiment, the invention provides a phenol compound of Formula (X)

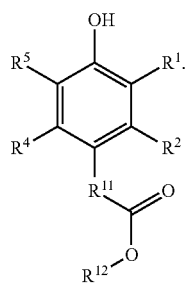

(I)

In the structure of Formula (X), $R^1$, $R^2$, $R^4$, and $R^5$ are independently selected from the group consisting of hydrogen, hydroxy groups, alkyl groups, substituted alkyl groups, cycloalkyl groups, substituted cycloalkyl groups, aryl groups, substituted aryl groups, heteroaryl groups, substituted heteroaryl groups, alkoxy groups, substituted alkoxy groups, aryloxy groups, and substituted aryloxy groups. $R^{11}$ is an alkanediyl group, preferably a $C_1$-$C_8$ alkanediyl group, more preferably a $C_1$-$C_4$ alkanediyl group, and most preferably an ethane-1,2-diyl group. $R^{12}$ is —$R^yR^x$ or —$R^zR^yR^x$, where $R^x$ is selected from the group consisting of hydrogen and alkyl, $R^z$ is selected from the group consisting of alkoxy groups (e.g., $C_1$-$C_4$ alkoxy groups) and substituted alkoxy groups (e.g., $C_1$-$C_4$ substituted alkoxy groups), and $R^y$ is a polymeric substituent of Formula (C), (CX), (CXX), (CXXX), (CXL), (CL), (CLX), or (CLXX) or a polymeric substituent comprising two or more groups of Formula (C), (CX), (CXX), (CXXX), (CXL), (CL), (CLX), or (CLXX) covalently bonded together. Preferably, $R^1$ and $R^5$ are independently selected alkyl groups (preferably $C_1$-$C_8$ alkyl groups, and more preferably tert-butyl groups), $R^2$ and $R^4$ are hydrogen, $R^x$ is selected from the group consisting of hydrogen and alkyl (e.g., $C_1$-$C_{10}$ alkyl or $C_1$-$C_4$ alkyl), and $R^y$ is a polymeric substituent of Formula (C) or Formula (CX).

In a particularly preferred embodiment of the structure of Formula (X), $R^1$ and $R^5$ are independently selected alkyl groups (preferably $C_1$-$C_8$ alkyl groups, and more preferably tert-butyl groups), $R^2$ and $R^4$ are hydrogen, $R^{11}$ is a $C_1$-$C_4$ alkanediyl group (most preferably an ethane-1,2-diyl group), $R^{12}$ is —$R^zR^yR^x$, $R^x$ is selected from the group consisting of hydrogen and alkyl (e.g., $C_1$-$C_{10}$ alkyl or $C_1$-$C_4$ alkyl), $R^z$ is selected from the group consisting of $C_1$-$C_4$ alkoxy groups (preferably, an ethoxy group), and $R^y$ is a polymeric substituent of Formula (CX).

In another preferred embodiment of the structure of Formula (X), $R^1$ and $R^5$ are independently selected alkyl groups (preferably $C_1$-$C_8$ alkyl groups, and more preferably tert-butyl groups), $R^2$ and $R^4$ are hydrogen, $R^{11}$ is a $C_1$-$C_4$ alkanediyl group (most preferably an ethane-1,2-diyl group), $R^{12}$ is —$R^yR^x$, $R^x$ is selected from the group consisting of hydrogen and alkyl (preferably $C_1$-$C_4$ alkyl, most preferably methyl), and $R^y$ is a polymeric substituent of Formula (C).

In another preferred embodiment, the invention provides a phenol compound of Formula (XX)

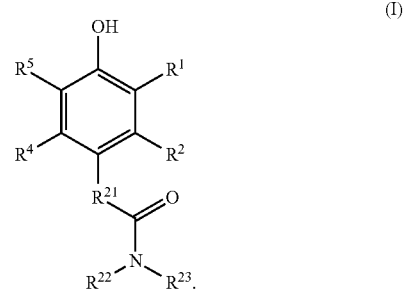

(I)

In the structure of Formula (XX), $R^1$, $R^2$, $R^4$, and $R^5$ are independently selected from the group consisting of hydrogen, hydroxy groups, alkyl groups, substituted alkyl groups, cycloalkyl groups, substituted cycloalkyl groups, aryl groups, substituted aryl groups, heteroaryl groups, substituted heteroaryl groups, alkoxy groups, substituted alkoxy groups, aryloxy groups, and substituted aryloxy groups. $R^{21}$ is an alkanediyl group, preferably a $C_1$-$C_8$ alkanediyl group, more preferably a $C_1$-$C_4$ alkanediyl group, and most preferably an ethane-1,2-diyl group. $R^{22}$ and $R^{23}$ are independently selected from the group consisting of hydrogen, —$R^yR^x$, and —$R^zR^yR^x$, where $R^x$ is selected from the group consisting of hydrogen and alkyl, $R^z$ is selected from the group consisting of alkoxy groups (e.g., $C_1$-$C_4$ alkoxy groups) and substituted alkoxy groups (e.g., $C_1$-$C_4$ substituted alkoxy groups), and $R^y$ is a polymeric substituent of Formula (C), (CX), (CXX), (CXXX), (CXL), (CL), (CLX), or (CLXX) or a polymeric substituent comprising two or more groups of Formula (C), (CX), (CXX), (CXXX), (CXL), (CL), (CLX), or (CLXX) covalently bonded together. In the structure of Formula (XX), at least one of $R^{22}$ and $R^{23}$ is —$R^yR^x$ or —$R^zR^yR^x$. Preferably, $R^1$ and $R^5$ are independently selected alkyl groups (preferably $C_1$-$C_8$ alkyl groups, and more preferably tert-butyl groups), $R^2$ and $R^4$ are hydrogen, $R^x$ is selected from the group consisting of hydrogen and alkyl (e.g., $C_1$-$C_{10}$ alkyl or $C_1$-$C_4$ alkyl), and $R^y$ is a polymeric substituent of Formula (C) or Formula (CX).

In a particularly preferred embodiment of the structure of Formula (XX), $R^1$ and $R^5$ are independently selected alkyl groups (preferably $C_1$-$C_8$ alkyl groups, and more preferably tert-butyl groups), $R^2$ and $R^4$ are hydrogen, $R^{21}$ is a $C_1$-$C_4$ alkanediyl group (most preferably an ethane-1,2-diyl group), $R^{22}$ is hydrogen, $R^{23}$ is —$R^zR^yR^x$, $R^x$ is selected from the group consisting of hydrogen and alkyl (e.g., $C_1$-$C_{10}$ alkyl or $C_1$-$C_4$ alkyl), $R^z$ is selected from the group consisting of $C_1$-$C_4$ alkoxy groups (preferably, an ethoxy group), and $R^y$ is a polymeric substituent of Formula (CX).

In another preferred embodiment of the structure of Formula (XX), $R^1$ and $R^5$ are independently selected alkyl groups (preferably $C_1$-$C_8$ alkyl groups, and more preferably tert-butyl groups), $R^2$ and $R^4$ are hydrogen, $R^{21}$ is a $C_1$-$C_4$ alkanediyl group (most preferably an ethane-1,2-diyl group), $R^{22}$ is hydrogen, $R^{23}$ is —$R^y R^x$, $R^x$ is selected from the group consisting of hydrogen and alkyl (preferably $C_1$-$C_4$ alkyl, most preferably methyl), and $R^y$ is a polymeric substituent of Formula (C).

In another preferred embodiment of the structure of Formula (XX), $R^1$ and $R^5$ are independently selected alkyl groups (preferably $C_1$-$C_8$ alkyl groups, and more preferably tert-butyl groups), $R^2$ and $R^4$ are hydrogen, $R^{21}$ is a $C_1$-$C_4$ alkanediyl group (most preferably an ethane-1,2-diyl group), $R^{22}$ is hydrogen, $R^{23}$ is —$R^y R^x$, $R^x$ is hydrogen, and $R^y$ is a polymeric substituent comprising monomer units of Formula (C) and Formula (CX) covalently bound to each other.

In the structures above, any charge present in any of the structures is balanced with a suitable independently selected internal or external counterion. Suitable independently selected external counterions may be cationic or anionic. Examples of suitable cations include but are not limited to one or more metals preferably selected from Group I and Group II, the most preferred of these being Na, K, Mg, and Ca, or an organic cation such as iminium, ammonium, and phosphonium. Examples of suitable anions include but are not limited to: fluoride, chloride, bromide, iodide, perchlorate, hydrogen sulfate, sulfate, aminosulfate, nitrate, dihydrogen phosphate, hydrogen phosphate, phosphate, bicarbonate, carbonate, methosulfate, ethosulfate, cyanate, thiocyanate, tetrachlorozincate, borate, tetrafluoroborate, acetate, chloroacetate, cyanoacetate, hydroxyacetate, aminoacetate, methylaminoacetate, di- and tri-chloroacetate, 2-chloro-propionate, 2-hydroxypropionate, glycolate, thioglycolate, thioacetate, phenoxyacetate, trimethylacetate, valerate, palmitate, acrylate, oxalate, malonate, crotonate, succinate, citrate, methylene-bis-thioglycolate, ethylene-bis-iminoacetate, nitrilotriacetate, fumarate, maleate, benzoate, methylbenzoate, chlorobenzoate, dichlorobenzoate, hydroxybenzoate, aminobenzoate, phthalate, terephthalate, indolylacetate, chlorobenzenesulfonate, benzenesulfonate, toluenesulfonate, biphenyl-sulfonate and chlorotoluenesulfonate. Those of ordinary skill in the art are well aware of different counterions which can be used in place of those listed above.

The phenol compounds described above are believed to be well-suited for use as antioxidants or stabilizers for organic materials that are subject to oxidative or other degradation. Specifically, the phenol compounds are believed to be effective free radical scavengers, which function by donating a hydrogen atom (i.e., the hydrogen atom from the hydroxy group) to the free radical species. Thus, in one application, the phenol compounds described above can be used as antioxidants or stabilizers for organic polymers, such as polyolefin and polyurethane polymers, and for compositions containing organic components that are susceptible to degradation, such as laundry care compositions. In such applications, the phenol compounds can be tailored to have characteristics that optimize their performance in the polymer or composition to which they are added. For instance, the length of the polymeric substituent can be tailored to improve the compatibility of the phenol compound with the components of the composition or, in the case of a stabilizing a polymer, the polymer itself or the raw materials used in making the polymer. For example, the length of the polymeric substituent can be tailored to yield a phenol compound that is liquid at ambient temperatures, making it easier to handle and homogeneously blend the phenol compound with the liquid raw materials (e.g., polyols) used in making certain polymers (e.g., polyurethane polymers). Also, the polymeric substituent can contain one or more functional groups that react into the polymer, thereby grafting the antioxidant phenol compound onto the polymer backbone. In such an embodiment, the phenol compound's polymeric substituent can have one reactive functional group, which will make the phenol compound function as a chain terminating agent, or the polymeric substituent can have two or more reactive functional groups, which will allow the phenol compound to function as a chain extender or a cross-linking agent. By incorporating the phenol compound into the polymer, the phenol compound cannot migrate out of the polymer, which addresses one of the drawbacks to the use of known phenol antioxidants in polymers.

In a second embodiment, the invention provides a method for producing a polyurethane polymer using the above-described phenol compound as an antioxidant or stabilizer. The method comprises the steps of: (a) providing a polyol; (b) providing a polyisocyanate compound; (c) providing a phenol compound as described above; (d) combining the polyol, the polyisocyanate compound, and the phenol compound to produce a reaction mixture; and (e) allowing the polyol and the polyisocyanate compound to react to produce a polyurethane polymer.

The method described above can utilize any suitable polyol or combination of polyols. Suitable polyols include, but are not limited to, glycols of low molecular weight, such as ethylene glycol, 1,2-propylene glycol, 1,3-propylene glycol, 1,4-butylene glycol, and 1,6-hexamethylene glycol; polyester diols obtained from dibasic acids, such as adipic acid, maleic acid, and terephthalic acid; polyester diols, such as polylactones obtained by subjecting lactones to ring-opening polymerization with glycols; polycarbonate diols; and polyether diols, such as polytetramethylene glycol, polyethylene glycol, and polypropylene glycol. Suitable polyether polyols include those made by reacting epoxides, such as ethylene oxide, propylene oxide, butylene oxide, and glycidol, with a multifunctional initiator compound, such as a multifunctional alcohol or amine. Examples of suitable multifunctional initiator compounds include, but are not limited to, water, glycerin, pentaerythritol, ethylene glycol, propylene glycol (e.g., 1,2-propylene glycol), trimethylolpropane, sugars, and ethylene diamine. The polyol(s) used in the method can have any suitable molar mass. In a preferred embodiment, the polyol(s) has a molar mass of about 400 g/mol or more. More preferably, the polyol(s) has a molar mass of about 500 g/mol or more, about 750 g/mol or more, or about 1,000 g/mol or more. Preferably, the polyol(s) has a molar mass of about 10,000 g/mol or less. Thus, the polyol(s) has a molar mass of about 400 g/mol to about 10,000 g/mol, about 500 g/mol to about 10,000 g/mol, about 750 g/mol to about 10,000 g/mol, or about 1,000 g/mol to about 10,000 g/mol.

The method described above can utilize any suitable polyisocyanate compound or combination of polyisocyanate compounds. Suitable polyisocyanate compounds include, but are not limited to, aromatic diisocyanates, such as toluene-2,4-diisocyanate (TDI), 4-methoxy-1,3-phenylene diisocyanate, 4-isopropyl-1,3-phenylene diisocyanate, 4-chloro-1,3-phenylene diisocyanate, 4-butoxy-1,3-phenylene diisocyanate, 2,4-diisocyanatodiphenyl ether, 4,4'-methylenebis(phenyl-isocyanate) (MDI), polymeric MDI, durylene diisocyanate, tolidine diisocyanate, xylylene diisocyanate (XDI), 1,5-naphthalene diisocyanate, benzidine diisocyanate, o-nitrobenzidine diisocyanate, and 4,4-diisocyanatodibenzyl; aliphatic diisocyanates, such as methylene diisocyanate, 1,4-tetramethylene diisocyanate, 1,6-hexamethylene diisocyanate, and 1,10-decamethylene diisocyanate; alicyclic diisocyanates, such as 1,4-cyclohexylene diisocyanate, 4,4-methylene-bis(cyclohexylisocyanate), 1,5-tetrahydronaphthalene diisocyanate, isophorone diisocyanate, hydrogenated MDI, and hydrogenated XDI; and polyurethane prepolymers obtained by reacting any of the aforementioned diisocyanates with polyols or polyamines of low molecular weights such that the resulting prepolymers have isocyanate groups at ends thereof.

In addition to the polyol(s) and the polyisocyanate compound(s), the reaction mixture can contain one or more suitable chain extenders. These include, but are not limited to, water; low-molecular diols, such as ethylene glycol and propylene glycol; aliphatic diamines, such as ethylenediamine; aromatic diamines, such as 4,4'-diaminodiphenylmethane; alicyclic diamines, such as 4,4'-diaminodicyclohexylmethane and isophoronediamine; alkanolamines, such as ethanolamine; hydrazines; and dihydrazides, such as succinic dihydrazide. Among the aforementioned chain extenders, the diamine compounds are preferable, with 4,4'-diaminodiphenylmethane being particularly preferred due to its heat resistance and 4,4'-diaminodicyclohexylmethane being preferred for light resistance. The aforementioned chain extenders can, of course, be used alone or in any suitable combination.

When the method is used to produce a polyurethane foam, the reaction mixture preferably comprises one or more suitable blowing agent(s). Suitable blowing agents include, but are not limited to, pentane, 1,1,1,2-tetrafluoroethane, 1,1,1,3,3-pentafluoropropane, water (which produces carbon dioxide through a reaction with the polyisocyanate compound), Typically, the polyol(s) and the polyisocyanate compound(s) are reacted in the presence of a catalyst, such as an amine catalyst, an organometallic catalyst (e.g., organotin compounds, such as dibutyltin dilaurate), or a mixture of the two. Amine catalysts, which are typically tertiary amine compounds (e.g., triethylenediamine or 1,4-diazabicyclo [2.2.2]octane, dimethylcyclohexylamine, dimethylethanolamine, and bis-(2-dimethylaminoethyl)ether), are the most commonly used catalysts in the production of flexible polyurethane foams, such as those used in seating and other cushioning applications.

In the method described above, the above-described phenol compound(s) can be added into the reaction system at any suitable level. As will be understood by those skilled in the art, the requisite loading of the phenol compound(s) will depend upon several factors, such as the molar mass of the phenol compound(s), the particular polyol that is being used, and the level of antioxidant protection desired for the resulting polyurethane polymer. Typically, the phenol compound(s) are added to the reaction system in an amount of about 10 parts by weight per one hundred parts by weight of the polyol (php) or less. Thus, in a preferred embodiment, the phenol compound(s) preferably are added to the reaction system in an amount of about 0.04 to about 5 php or more preferably from about 0.04 to 3 php. When more than one of the above-described phenol compounds is used, each phenol compound can be added to the reaction mixture in an amount falling within one of the ranges recited above, or the total amount of the above-described phenol compounds added to the reaction mixture can fall within one of the ranges recited above. Preferably, the total amount of the above-described phenol compounds added to the reaction mixture falls within one of the ranges recited above.

In a third embodiment, the invention provides a laundry care composition comprising one or more of the phenol compounds described above. More specifically, in this embodiment, the invention provides a laundry care composition comprising one or more laundry care ingredients and one or more of the phenol compounds described above.

The phenol compound(s) described above can be present in the laundry care composition in any suitable amount. For example, the phenol compound(s) can be present in the laundry care composition in an amount of about 0.001 to about 2% by weight. Preferably, the phenol compound(s) are present in the laundry care composition at a concentration in the range of 0.01 to 0.08% by weight. When the laundry care composition contains more than one of the above-described phenol compounds, each phenol compound can be individually present in the laundry care composition in an amount falling within one of the ranges recited above, or the combined amount of all the phenol compounds present in the composition can fall within one of the ranges recited above. Preferably, the combined amount of all the phenol compounds present in the composition (i.e., all the phenol compounds described above) falls within one of the ranges recited above.

Laundry Care Ingredients

Surfactant System

The laundry care compositions of the present invention may comprise from about 0.00 wt %, more typically from about 0.10 to 80% by weight of a surfactant. In one aspect, such compositions may comprise from about 5% to 50% by weight of surfactant. Surfactants utilized can be of the anionic, nonionic, amphoteric, ampholytic, zwitterionic, or cationic type or can comprise compatible mixtures of these types. Anionic and nonionic surfactants are typically employed if the fabric care product is a laundry detergent. On the other hand, cationic surfactants are typically employed if the fabric care product is a fabric softener.

Anionic Surfactant

Useful anionic surfactants can themselves be of several different types. For example, water-soluble salts of the higher fatty acids, i.e., "soaps", are useful anionic surfactants in the compositions herein. This includes alkali metal soaps such as the sodium, potassium, ammonium, and alkylolammonium salts of higher fatty acids containing from about 8 to about 24 carbon atoms, or even from about 12 to about 18 carbon atoms. Soaps can be made by direct saponification of fats and oils or by the neutralization of free fatty acids. Particularly useful are the sodium and potassium salts of the mixtures of fatty acids derived from coconut oil and tallow, i.e., sodium or potassium tallow and coconut soap.

Preferred alkyl sulphates are C8-18 alkyl alkoxylated sulphates, preferably a C12-15 alkyl or hydroxyalkyl alkoxylated sulphates. Preferably the alkoxylating group is an ethoxylating group. Typically the alkyl alkoxylated sulphate has an average degree of alkoxylation from 0.5 to 30 or 20, or from 0.5 to 10. The alkyl group may be branched or linear. The alkoxylated alkyl sulfate surfactant may be a mixture of alkoxylated alkyl sulfates, the mixture having an average (arithmetic mean) carbon chain length within the range of about 12 to about 30 carbon atoms, or an average carbon chain length of about 12 to about 15 carbon atoms, and an average (arithmetic mean) degree of alkoxylation of from about 1 mol to about 4 mols of ethylene oxide, propylene oxide, or mixtures thereof, or an average (arithmetic mean) degree of alkoxylation of about 1.8 mols of ethylene oxide, propylene oxide, or mixtures thereof. The alkoxylated alkyl sulfate surfactant may have a carbon chain length from about 10 carbon atoms to about 18 carbon atoms, and a degree of alkoxylation of from about 0.1 to about 6 mols of ethylene oxide, propylene oxide, or mixtures thereof. The alkoxylated alkyl sulfate may be alkoxylated with ethylene oxide, propylene oxide, or mixtures thereof. Alkyl ether sulfate surfactants may contain a peaked ethoxylate distribution. Specific example include C12-C15 EO 2.5 Sulfate, C14-C15 EO 2.5 Sulfate and C12-C15 EO 1.5 Sulfate derived from NEODOL® alcohols from Shell and C12-C14 EO3 Sulfate, C12-C16 EO3 Sulfate, C12-C14 EO2 Sulfate and C12-C14 EO1 Sulfate derived from natural alcohols from Huntsman. The AES may be linear, branched, or combinations thereof. The alkyl group may be derived from synthetic or natural alcohols such as those supplied by the tradename Neodol® by Shell, Safol®, Lial®, and Isalchem® by Sasol or midcut alcohols derived from vegetable oils such as coconut and palm kernel. Another suitable anionic detersive surfactant is alkyl ether carboxylate, comprising a C10-C26 linear or branched, preferably C10-C20 linear, most preferably C16-C18 linear alkyl alcohol and from 2 to 20, preferably 7 to 13, more preferably 8 to 12, most preferably 9.5 to 10.5 ethoxylates. The acid form or salt form, such as sodium or ammonium salt, may be used, and the alkyl chain may contain one cis or trans double bond. Alkyl ether carboxylic acids are available from Kao (Akypo®), Huntsman (Empicol®) and Clariant (Emulsogen®).

Other useful anionic surfactants can include the alkali metal salts of alkyl benzene sulfonates, in which the alkyl group contains from about 9 to about 15 carbon atoms, in straight chain (linear) or branched chain configuration. In some examples, the alkyl group is linear. Such linear alkylbenzene sulfonates are known as "LAS." In other examples, the linear alkylbenzene sulfonate may have an average number of carbon atoms in the alkyl group of from about 11 to 14. In a specific example, the linear straight chain alkylbenzene sulfonates may have an average number of carbon atoms in the alkyl group of about 11.8 carbon atoms, which may be abbreviated as C11.8 LAS. Preferred sulphonates are C10-13 alkyl benzene sulphonate. Suitable alkyl benzene sulphonate (LAS) may be obtained, by sulphonating commercially available linear alkyl benzene (LAB); suitable LAB includes low 2-phenyl LAB, such as those supplied by Sasol under the tradename Isochem® or those supplied by Petresa under the tradename Petrelab®, other suitable LAB include high 2-phenyl LAB, such as those supplied by Sasol under the tradename Hyblene®. A suitable anionic detersive surfactant is alkyl benzene sulphonate that is obtained by DETAL catalyzed process, although other synthesis routes, such as HF, may also be suitable. In one aspect a magnesium salt of LAS is used. Suitable anionic sulfonate surfactants for use herein include water-soluble salts of C8-C18 alkyl or hydroxyalkyl sulfonates; C11-C18 alkyl benzene sulfonates (LAS), modified alkylbenzene sulfonate (MLAS) as discussed in WO 99/05243, WO 99/05242, WO 99/05244, WO 99/05082, WO 99/05084, WO 99/05241, WO 99/07656, WO 00/23549, and WO 00/23548; methyl ester sulfonate (MES); and alpha-olefin sulfonate (AOS). Those also include the paraffin sulfonates may be monosulfonates and/or disulfonates, obtained by sulfonating paraffins of 10 to 20 carbon atoms. The sulfonate surfactant may also include the alkyl glyceryl sulfonate surfactants.

Anionic surfactants of the present invention may exist in an acid form, and said acid form may be neutralized to form a surfactant salt which is desirable for use in the present detergent compositions. Typical agents for neutralization include the metal counterion base such as hydroxides, e.g., NaOH or KOH. Further preferred agents for neutralizing anionic surfactants of the present invention and adjunct anionic surfactants or cosurfactants in their acid forms include ammonia, amines, or alkanolamines. Alkanolamines are preferred. Suitable non-limiting examples including monoethanolamine, diethanolamine, triethanolamine, and other linear or branched alkanolamines known in the art; for example, highly preferred alkanolamines include 2-amino-1-propanol, 1-aminopropanol, monoisopropanolamine, or 1-amino-3-propanol.

Nonionic Surfactant

Preferably, the laundry care composition comprises a nonionic detersive surfactant. Suitable nonionic surfactants include alkoxylated fatty alcohols. The nonionic surfactant may be selected from ethoxylated alcohols and ethoxylated alkyl phenols of the formula R(OC2H4), OH, wherein R is selected from the group consisting of aliphatic hydrocarbon radicals containing from about 8 to about 15 carbon atoms and alkyl phenyl radicals in which the alkyl groups contain from about 8 to about 12 carbon atoms, and the average value of n is from about 5 to about 15. Other non-limiting examples of nonionic surfactants useful herein include: C8-C18 alkyl ethoxylates, such as, NEODOL® nonionic surfactants from Shell; C6-C12 alkyl phenol alkoxylates where the alkoxylate units may be ethyleneoxy units, propyleneoxy units, or a mixture thereof; C12-C18 alcohol and C6-C12 alkyl phenol condensates with ethylene oxide/propylene oxide block polymers such as Pluronic® from BASF; C14-C22 mid-chain branched alcohols, BA; C14-C22 mid-chain branched alkyl alkoxylates, BAEx, wherein x is from 1 to 30; alkylpolysaccharides; specifically alkylpolyglycosides; polyhydroxy fatty acid amides; and ether capped poly(oxyalkylated) alcohol surfactants. Specific example include C12-C15 EO7 and C14-C15 EO7 NEODOL® nonionic surfactants from Shell, C12-C14 EO7 and C12-C14 EO9 Surfonic® nonionic surfactants from Huntsman.

Highly preferred nonionic surfactants are the condensation products of Guerbet alcohols with from 2 to 18 moles, preferably 2 to 15, more preferably 5-9 of ethylene oxide per mole of alcohol. Suitable nonionic surfactants include those with the trade name Lutensol® from BASF. Lutensol XP-50 is a Guerbet ethoxylate that contains an average of about 5 ethoxy groups. Lutensol XP-80 and containing an average of about 8 ethoxy groups. Other suitable non-ionic surfactants for use herein include fatty alcohol polyglycol ethers, alkylpolyglucosides and fatty acid glucamides, alkylpolyglucosides based on Guerbet alcohols.

Amphoteric Surfactant

The surfactant system may include amphoteric surfactant, such as amine oxide. Preferred amine oxides are alkyl dimethyl amine oxide or alkyl amido propyl dimethyl amine oxide, more preferably alkyl dimethyl amine oxide and especially coco dimethyl amino oxide. Amine oxide may have a linear or mid-branched alkyl moiety.

Ampholytic Surfactants

The surfactant system may comprise an ampholytic surfactant. Specific, non-limiting examples of ampholytic surfactants include: aliphatic derivatives of secondary or tertiary amines, or aliphatic derivatives of heterocyclic secondary and tertiary amines in which the aliphatic radical can be straight- or branched-chain. One of the aliphatic substituents may contain at least about 8 carbon atoms, for example from about 8 to about 18 carbon atoms, and at least one contains an anionic water-solubilizing group, e.g. carboxy, sulfonate, sulfate. See U.S. Pat. No. 3,929,678 at column 19, lines 18-35, for suitable examples of ampholytic surfactants.

Zwitterionic Surfactant

Zwitterionic surfactants are known in the art, and generally include surfactants which are neutrally charged overall, but carry at least one positive charged atom/group and at least one negatively charged atom/group. Examples of zwitterionic surfactants include: derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 at column 19, line 38 through column 22, line 48, for examples of zwitterionic surfactants; betaines, including alkyl dimethyl betaine and cocodimethyl amidopropyl betaine, $C_8$ to $C_{18}$ (for example from $C_{12}$ to $C_{18}$) amine oxides and sulfo and hydroxy betaines, such as N-alkyl-N,N-dimethylammino-1-propane sulfonate where the alkyl group can be $C_8$ to $C_{18}$ and in certain embodiments from $C_{10}$ to $C_{14}$. A preferred zwitterionic surfactant for use in the present invention is the cocoamidopropyl betaine.

Cationic Surfactants

Examples of cationic surfactants include quaternary ammonium surfactants, which can have up to 26 carbon atoms specific. Additional examples include a) alkoxylate quaternary ammonium (AQA) surfactants as discussed in U.S. Pat. No. 6,136,769; b) dimethyl hydroxyethyl quaternary ammonium as discussed in U.S. Pat. No. 6,004,922; c) polyamine cationic surfactants as discussed in WO 98/35002, WO 98/35003, WO 98/35004, WO 98/35005, and WO 98/35006, which is herein incorporated by reference; d) cationic ester surfactants as discussed in U.S. Pat. Nos. 4,228,042, 4,239,660 4,260,529 and U.S. Pat. No. 6,022,844, which is herein incorporated by reference; and e) amino surfactants as discussed in U.S. Pat. No. 6,221,825 and WO 00/47708, which is herein incorporated by reference, and specifically amido propyldimethyl amine (APA). Useful cationic surfactants also include those described in U.S. Pat. No. 4,222,905, Cockrell, issued Sep. 16, 1980, and in U.S. Pat. No. 4,239,659, Murphy, issued Dec. 16, 1980, both of which are also incorporated herein by reference. Quaternary ammonium compounds may be present in fabric enhancer compositions, such as fabric softeners, and comprise quaternary ammonium cations that are positively charged polyatomic ions of the structure $NR_4+$, where R is an alkyl group or an aryl group.

Adjunct Cleaning Additives

The laundry care compositions of the invention may also contain adjunct cleaning additives. The precise nature of the cleaning adjunct additives and levels of incorporation thereof will depend on the physical form of the laundry care composition, and the precise nature of the cleaning operation for which it is to be used.

The adjunct cleaning additives may be selected from the group consisting of builders, structurants or thickeners, clay soil removal/anti-redeposition agents, polymeric soil release agents, polymeric dispersing agents, polymeric grease cleaning agents, enzymes, enzyme stabilizing systems, bleaching compounds, bleaching agents, bleach activators, bleach catalysts, brighteners, dyes, hueing agents, dye transfer inhibiting agents, chelating agents, suds supressors, softeners, and perfumes. This listing of adjunct cleaning additives is exemplary only, and not by way of limitation of the types of adjunct cleaning additives which can be used. In principle, any adjunct cleaning additive known in the art may be used in the instant invention.

Polymers

The composition may comprise one or more polymers. Non-limiting examples, all of which may be optionally modified, include polyethyleneimines, carboxymethylcellulose, poly(vinyl-pyrrolidone), poly (ethylene glycol), poly (vinyl alcohol), poly(vinylpyridine-N-oxide), poly(vinylimidazole), polycarboxylates or alkoxylated substituted phenols (ASP). as described in WO 2016/041676. An example of ASP dispersants, include but are not limited to, HOSTAPAL BV CONC S1000 available from Clariant.

Polyamines may be used for grease, particulate removal or stain removal. A wide variety of amines and polyaklyeneimines can be alkoxylated to various degrees to achieve hydrophobic or hydrophilic cleaning. Such compounds may include, but are not limited to, ethoxylated polyethyleneimine, ethoxylated hexamethylene diamine, and sulfated versions thereof. Useful examples of such polymers are HP20 available from BASF or a polymer having the following general structure:

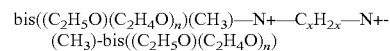

wherein n=from 20 to 30, and x=from 3 to 8, or sulphated or sulphonated variants thereof. Polypropoxylated-polyethoxylated amphiphilic polyethyleneimine derivatives may also be included to achieve greater grease removal and emulsification. These may comprise alkoxylated polyalkylenimines, preferably having an inner polyethylene oxide block and an outer polypropylene oxide block. Detergent compositions may also contain unmodified polyethyleneimines useful for enhanced beverage stain removal. PEI's of various molecular weights are commercially available from the BASF Corporation under the trade name Lupasol® Examples of suitable PEI's include, but are not limited to, Lupasol FG®, Lupasol G-35®.

The composition may comprise one or more carboxylate polymers, such as a maleate/acrylate random copolymer or polyacrylate homopolymer useful as polymeric dispersing agents. Alkoxylated polycarboxylates such as those prepared from polyacrylates are also useful to provide clay dispersancy. Such materials are described in WO 91/08281. Chemically, these materials comprise polyacrylates having one ethoxy side-chain per every 7-8 acrylate units. The side-chains are of the formula $-(CH_2CH_2O)_m (CH_2)_nCH_3$ wherein m is 2-3 and n is 6-12. The side-chains are ester or ether-linked to the polyacrylate "backbone" to provide a "comb" polymer type structure.

Preferred amphiphilic graft co-polymer(s) comprise (i) polyethyelene glycol backbone; and (ii) at least one pendant moiety selected from polyvinyl acetate, polyvinyl alcohol and mixtures thereof. An example of an amphiphilic graft co-polymer is Sokalan HP22, supplied from BASF.

Alkoxylated substituted phenols as described in WO 2016/041676 are also suitable examples of polymers that provide clay dispersancy. Hostapal BV Conc S1000, available from Clariant, is one non-limiting example of an ASP dispersant.

Preferably the composition comprises one or more soil release polymers. Suitable soil release polymers are polyester soil release polymers such as Repel-o-tex polymers, including Repel-o-tex SF, SF-2 and SRP6 supplied by Rhodia. Other suitable soil release polymers include Texcare polymers, including Texcare SRA100, SRA300, SRN100, SRN170, SRN240, SRN260 SRN300 and SRN325 supplied by Clariant. Other suitable soil release polymers are Marloquest polymers, such as Marloquest SL, HSCB, L235M, B, G82 supplied by Sasol. Other suitable soil release polymers include methyl-capped ethoxylated propoxylated soil release polymers as described in U.S. Pat. No. 9,365,806.

Preferably the composition comprises one or more polysaccharides which may in particular be chosen from carboxymethyl cellulose, methylcarboxymethylcellulose, sulfoethylcellulose, methylhydroxyethylcellulose, carboxymethyl xyloglucan, carboxymethyl xylan, sulfoethylgalactomannan, carboxymethyl galactomannan, hydoxyethyl galactomannan, sulfoethyl starch, carboxymethyl starch, and mixture thereof. Other polysaccharides suitable for use in the present invention are the glucans. Preferred glucans are Poly alpha-1,3-glucan which is a polymer comprising glucose monomeric units linked together by glycosidic linkages (i.e., glucosidic linkages), wherein at least about 50% of the glycosidic linkages are alpha-1,3-glycosidic linkages. Poly alpha-1,3-glucan is a type of polysaccharide. Poly alpha-1,3-glucan can be enzymatically produced from sucrose using one or more glucosyltransferase enzymes, such as described in U.S. Pat. No. 7,000,000, and U.S. Patent Appl. Publ. Nos. 2013/0244288 and 2013/0244287 (all of which are incorporated herein by reference), for example.

Other suitable polysaccharides for use in the composition are cationic polysaccharides. Examples of cationic polysaccharides include cationic guar gum derivatives, quaternary nitrogen-containing cellulose ethers, and synthetic polymers that are copolymers of etherified cellulose, guar and starch. When used, the cationic polymers herein are either soluble in the composition or are soluble in a complex coacervate phase in the composition formed by the cationic polymer and the anionic, amphoteric and/or zwitterionic surfactant component described hereinbefore. Suitable cationic polymers are described in U.S. Pat. Nos. 3,962,418; 3,958,581; and U.S. Publication No. 2007/0207109A1.

Polymers can also function as deposition aids for other detergent raw materials. Preferred deposition aids are selected from the group consisting of cationic and nonionic polymers. Suitable polymers include cationic starches, cationic hydroxyethylcellulose, polyvinylformaldehyde, locust bean gum, mannans, xyloglucans, tamarind gum, polyethyleneterephthalate and polymers containing dimethylaminoethyl methacrylate, optionally with one or more monomers selected from the group comprising acrylic acid and acrylamide.

Additional Amines

Polyamines are known to improve grease removal. Preferred cyclic and linear amines for performance are 1,3-bis(methylamine)-cyclohexane, 4-methylcyclohexane-1,3-diamine (Baxxodur ECX 210 supplied by BASF) 1,3 propane diamine, 1,6 hexane diamine, 1,3 pentane diamine (Dytek EP supplied by Invista), 2-methyl 1,5 pentane diamine (Dytek A supplied by Invista). U.S. Pat. No. 6,710,023 discloses hand dishwashing compositions containing said diamines and polyamines containing at least 3 protonable amines. Polyamines according to the invention have at least one pka above the wash pH and at least two pka's greater than about 6 and below the wash pH. Preferred polyamines with are selected from the group consisting of tetraethylenepentamine, hexaethylhexamine, heptaethylheptamines, octaethyloctamines, nonethylnonamines, and mixtures thereof commercially available from Dow, BASF and Huntman. Especially preferred polyetheramines are lipophilic modified as described in U.S. Pat. Nos. 9,752,101, 9,487,739, 9,631,163

Dye Transfer Inhibitor (DTI)

The composition may comprise one or more dye transfer inhibiting agents. In one embodiment of the invention the inventors have surprisingly found that compositions comprising polymeric dye transfer inhibiting agents in addition to the specified dye give improved performance. This is surprising because these polymers prevent dye deposition. Suitable dye transfer inhibitors include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. Suitable examples include PVP-K15, PVP-K30, ChromaBond S-400, ChromaBond S-403E and Chromabond S-100 from Ashland Aqualon, and Sokalan HP165, Sokalan HP50, Sokalan HP53, Sokalan HP59, Sokalan® HP 56K, Sokalan® HP 66 from BASF. Other suitable DTIs are as described in WO2012/004134. When present in a subject composition, the dye transfer inhibiting agents may be present at levels from about 0.0001% to about 10%, from about 0.01% to about 5% or even from about 0.1% to about 3% by weight of the composition.

Enzymes

Enzymes may be included in the laundry care compositions for a variety of purposes, including removal of protein-based, carbohydrate-based, or triglyceride-based stains from substrates, for the prevention of refugee dye transfer in fabric laundering, and for fabric restoration. Suitable enzymes include proteases, amylases, lipases, carbohydrases, cellulases, oxidases, peroxidases, mannanases, and mixtures thereof of any suitable origin, such as vegetable, animal, bacterial, fungal, and yeast origin. Other enzymes that may be used in the laundry care compositions described herein include hemicellulases, peroxidases, proteases, cellulases, endoglucanases, xylanases, lipases, phospholipases, amylases, gluco-amylases, xylanases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidases, chondroitinases, laccases, or mixtures thereof, esterases, mannanases, pectate lyases, and or mixtures thereof. Other suitable enzymes include Nuclease enzyme. The composition may comprise a nuclease enzyme. The nuclease enzyme is an enzyme capable of cleaving the phosphodiester bonds between the nucleotide sub-units of nucleic acids. The nuclease enzyme herein is preferably a deoxyribonuclease or ribonuclease enzyme or a functional fragment thereof. Enzyme selection is influenced by factors such as pH-activity and/or stability optima, thermostability, and stability to active detergents, builders, and the like.

The enzymes may be incorporated into the laundry care composition at levels from 0.0001% to 5% of active enzyme by weight of the laundry care composition. The enzymes can be added as a separate single ingredient or as mixtures of two or more enzymes.

In some embodiments, lipase may be used. Lipase may be purchased under the trade name Lipex from Novozymes (Denmark). Amylases (Natalase®, Stainzyme®, Stainzyme Plus®) may be supplied by Novozymes, Bagsvaerd, Denmark. Proteases may be supplied by Genencor International, Palo Alto, Calif., USA (e.g. Purafect Prime®) or by Novozymes, Bagsvaerd, Denmark (e.g. Liquanase®, Coronase®, Savinase®). Other preferred enzymes include pectate lyases preferably those sold under the trade names Pectawash®, Xpect®, Pectaway® and the mannanases sold under the trade names Mannaway® (all from Novozymes A/S, Bagsvaerd, Denmark), and Purabrite® (Genencor International Inc., Palo Alto, Calif.). A range of enzyme materials and means for their incorporation into synthetic laundry care compositions is disclosed in WO 9307263 A; WO 9307260 A; WO 8908694 A; U.S. Pat. Nos. 3,553,139;

4,101,457; and 4,507,219. Enzyme materials useful for liquid laundry care compositions, and their incorporation into such compositions, are disclosed in U.S. Pat. No. 4,261,868.

Enzyme Stabilizing System

The enzyme-containing compositions described herein may optionally comprise from about 0.001% to about 10%, in some examples from about 0.005% to about 8%, and in other examples, from about 0.01% to about 6%, by weight of the composition, of an enzyme stabilizing system. The enzyme stabilizing system can be any stabilizing system which is compatible with the detersive enzyme. Such a system may be inherently provided by other formulation actives, or be added separately, e.g., by the formulator or by a manufacturer of detergent-ready enzymes. Such stabilizing systems can, for example, comprise calcium ion, boric acid, propylene glycol, short chain carboxylic acids, boronic acids, chlorine bleach scavengers and mixtures thereof, and are designed to address different stabilization problems depending on the type and physical form of the laundry care composition. See U.S. Pat. No. 4,537,706 for a review of borate stabilizers.

Chelating Agent

Preferably, the laundry care composition comprises chelating agents and/or crystal growth inhibitor. Suitable molecules include copper, iron and/or manganese chelating agents and mixtures thereof. Suitable molecules include aminocarboxylates, aminophosphonates, succinates, salts thereof, and mixtures thereof. Non-limiting examples of suitable chelants for use herein include ethylenediaminetetracetates, N-(hydroxyethyl)-ethylene-diamine-triacetates, nitrilotriacetates, ethylenediamine tetraprorionates, triethylene-tetraamine-hexacetates, diethylenetriamine-pentaacetates, ethanoldiglycines, ethylenediaminetetrakis (methylenephosphonates), diethylenetriamine penta(methylene phosphonic acid) (DTPMP), ethylenediamine disuccinate (EDDS), hydroxyethanedimethylenephosphonic acid (HEDP), methylglycinediacetic acid (MGDA), diethylenetriaminepentaacetic acid (DTPA), and 1,2-diydroxybenzene-3,5-disulfonic acid (Tiron), salts thereof, and mixtures thereof. Tiron as well as other sulphonated catechols may also be used as effective heavy metal chelants. Other non-limiting examples of chelants of use in the present invention are found in U.S. Pat. Nos. 7,445,644, 7,585,376 and 2009/0176684A1. Other suitable chelating agents for use herein are the commercial DEQUEST series, and chelants from Monsanto, DuPont, and Nalco Inc.

Brighteners

Optical brighteners or other brightening or whitening agents may be incorporated at levels of from about 0.01% to about 1.2%, by weight of the composition, into the laundry care compositions described herein. Commercial optical brighteners, which may be used herein, can be classified into subgroups, which include, but are not necessarily limited to, derivatives of stilbene, pyrazoline, coumarin, carboxylic acid, methinecyanines, dibenzothiphene-5,5-dioxide, azoles, 5- and 6-membered-ring heterocycles, and other miscellaneous agents. Examples of such brighteners are disclosed in "The Production and Application of Fluorescent Brightening Agents," M. Zahradnik, John Wiley & Sons, New York (1982). Specific, non-limiting examples of optical brighteners which may be useful in the present compositions are those identified in U.S. Pat. Nos. 4,790,856 and 3,646,015. Highly preferred Brighteners include Disodium 4,4'-bis({[4-anilino-6-[bis(2-hydroxyethyl)amino-s-triazin-2-yl]-amino}-2,2'-stilbenedisulfonate, 4,4'-bis{[4-anilino-6-morpholino-s-triazin-2-yl]-amino}-2,2'-stilbenedisulfonate, Disodium 4,4"-bis[(4,6-di-anilino-s-triazin-2-yl)-amino]-2,2'-stilbenedisulfonate and disodium 4,4'-bis-(2-sulfostyryl) biphenyl.

Bleaching Agents

It may be preferred for the composition to comprise one or more bleaching agents. Suitable bleaching agents include photobleaches, hydrogen peroxide, sources of hydrogen peroxide, pre-formed peracids and mixtures thereof.

(1) photobleaches for example sulfonated zinc phthalocyanine sulfonated aluminium phthalocyanines, xanthene dyes and mixtures thereof;

(2) pre-formed peracids: Suitable preformed peracids include, but are not limited to compounds selected from the group consisting of pre-formed peroxyacids or salts thereof typically a percarboxylic acids and salts, percarbonic acids and salts, perimidic acids and salts, peroxymonosulfuric acids and salts, for example, Oxone®, and mixtures thereof. Suitable examples include peroxycarboxylic acids or salts thereof, or peroxysulphonic acids or salts thereof. Particularly preferred peroxyacids are phthalimido-peroxy-alkanoic acids, in particular ε-phthalimido peroxy hexanoic acid (PAP). Preferably, the peroxyacid or salt thereof has a melting point in the range of from 30° C. to 60° C.

(3) sources of hydrogen peroxide, for example, inorganic perhydrate salts, including alkali metal salts such as sodium salts of perborate (usually mono- or tetra-hydrate), percarbonate, persulphate, perphosphate, persilicate salts and mixtures thereof.

Fabric Shading Dyes

The fabric shading dye (sometimes referred to as hueing, bluing or whitening agents) typically provides a blue or violet shade to fabric. Such dye(s) are well known in the art and may be used either alone or in combination to create a specific shade of hueing and/or to shade different fabric types. The fabric shading dye may be selected from any chemical class of dye as known in the art, including but not limited to acridine, anthraquinone (including polycyclic quinones), azine, azo (e.g., monoazo, disazo, trisazo, tetrakisazo, polyazo), benzodifurane, benzodifuranone, carotenoid, coumarin, cyanine, diazahemicyanine, diphenylmethane, formazan, hemicyanine, indigoids, methane, naphthalimides, naphthoquinone, nitro, nitroso, oxazine, phthalocyanine, pyrazoles, stilbene, styryl, triarylmethane, triphenylmethane, xanthenes and mixtures thereof. The amount of adjunct fabric shading dye present in a laundry care composition of the invention is typically from 0.0001 to 0.05 wt % based on the total laundry care composition, preferably from 0.0001 to 0.005 wt %. Based on the wash liquor, the concentration of fabric shading dye typically is from 1 ppb to 5 ppm, preferably from 10 ppb to 500 ppb.

Suitable fabric shading dyes include small molecule dyes, polymeric dyes and dye-clay conjugates. Preferred fabric shading dyes are selected from small molecule dyes and polymeric dyes. Suitable small molecule dyes may be selected from the group consisting of dyes falling into the Colour Index (C.I., Society of Dyers and Colourists, Bradford, UK) classifications of Acid, Direct, Basic, Reactive, Solvent or Disperse dyes.

Suitable polymeric dyes include dyes selected from the group consisting of polymers containing covalently bound (sometimes referred to as conjugated) chromogens, (also known as dye-polymer conjugates), for example polymers with chromogen monomers co-polymerized into the backbone of the polymer and mixtures thereof. Preferred polymeric dyes comprise the optionally substituted alkoxylated dyes, such as alkoxylated triphenyl-methane polymeric colourants, alkoxylated carbocyclic and alkoxylated heterocyclic azo colourants including alkoxylated thiophene polymeric colourants, and mixtures thereof, such as the fabric-substantive colorants sold under the name of Liquitint® (Milliken, Spartanburg, S.C., USA).

Suitable dye clay conjugates include dye clay conjugates selected from the group comprising at least one cationic/basic dye and a smectite clay; a preferred clay may be selected from the group consisting of Montmorillonite clay, Hectorite clay, Saponite clay and mixtures thereof.

Pigments are well known in the art and may also be used in the laundry care compositions herein. Suitable pigments include C.I Pigment Blues 15 to 20, especially 15 and/or 16, C.I. Pigment Blue 29, C.I. Pigment Violet 15, Monastral Blue and mixtures thereof.

Builders

The laundry care compositions of the present invention may optionally comprise a builder. Builders selected from aluminosilicates and silicates assist in controlling mineral hardness in wash water, or to assist in the removal of particulate soils from surfaces. Suitable builders may be selected from the group consisting of phosphates polyphosphates, especially sodium salts thereof; carbonates, bicarbonates, sesquicarbonates, and carbonate minerals other than sodium carbonate or sesquicarbonate; organic mono-, di-, tri-, and tetracarboxylates, especially water-soluble non-surfactant carboxylates in acid, sodium, potassium or alkanolammonium salt form, as well as oligomeric or water-soluble low molecular weight polymer carboxylates including aliphatic and aromatic types; and phytic acid. These may be complemented by borates, e.g., for pH-buffering purposes, or by sulfates, especially sodium sulfate and any other fillers or carriers which may be important to the engineering of stable surfactant and/or builder-containing laundry care compositions.

pH Buffer System

The laundry care compositions may also include a pH buffer system. The laundry care compositions herein may be formulated such that, during use in aqueous cleaning operations, the wash water will have a pH of between about 6.0 and about 12, and in some examples, between about 7.0 and 11. Techniques for controlling pH at recommended usage levels include the use of buffers, alkalis, or acids, and are well known to those skilled in the art. These include, but are not limited to, the use of sodium carbonate, citric acid or sodium citrate, monoethanol amine or other amines, boric acid or borates, and other pH-adjusting compounds well known in the art. The laundry care compositions herein may comprise dynamic in-wash pH profiles by delaying the release of citric acid.

Structurant/Thickeners

Structured liquids can either be internally structured, whereby the structure is formed by primary ingredients (e.g. surfactant material) and/or externally structured by providing a three dimensional matrix structure using secondary ingredients (e.g. polymers, clay and/or silicate material). The composition may comprise from about 0.01% to about 5%, by weight of the composition, of a structurant, and in some examples, from about 0.1% to about 2.0%, by weight of the composition, of a structurant. The structurant may be selected from the group consisting of diglycerides and triglycerides, ethylene glycol distearate, microcrystalline cellulose, cellulose-based materials, microfiber cellulose, biopolymers, xanthan gum, gellan gum, and mixtures thereof. In some examples, a suitable structurant includes hydrogenated castor oil, and non-ethoxylated derivatives thereof. Other suitable structurants are disclosed in U.S. Pat. No. 6,855,680. Such structurants have a thread-like structuring system having a range of aspect ratios. Further suitable structurants and the processes for making them are described in WO 2010/034736.

Suds Suppressors

Compounds for reducing or suppressing the formation of suds can be incorporated into the laundry care compositions described herein. Suds suppression can be of particular importance in the so-called "high concentration cleaning process" as described in U.S. Pat. Nos. 4,489,455, 4,489,574, and in front-loading style washing machines.

A wide variety of materials may be used as suds suppressors, and suds suppressors are well known to those skilled in the art. See, for example, Kirk Othmer Encyclopedia of Chemical Technology, Third Edition, Volume 7, pages 430-447 (John Wiley & Sons, Inc., 1979). Examples of suds suppressors include monocarboxylic fatty acid, and soluble salts therein, high molecular weight hydrocarbons such as paraffin, fatty acid esters (e.g., fatty acid triglycerides), fatty acid esters of monovalent alcohols, aliphatic $C_{18}$-$C_{40}$ ketones (e.g., stearone), N-alkylated amino triazines, waxy hydrocarbons preferably having a melting point below about 100° C., silicone suds suppressors, and secondary alcohols. Suds suppressors are described in U.S. Pat. Nos. 2,954,347; 4,075,118; 4,265,779; 4,265,779; 3,455,839; 3,933,672; 4,652,392; 4,978,471; 4,983,316; 5,288,431; 4,639,489; 4,749,740; and 4,798,679.

The laundry care compositions herein may comprise from 0% to about 10%, by weight of the composition, of suds suppressor. When utilized as suds suppressors, monocarboxylic fatty acids, and salts thereof, may be present in amounts up to about 5% by weight of the laundry care composition, and in some examples, may be from about 0.5% to about 3% by weight of the laundry care composition. Silicone suds suppressors may be utilized in amounts up to about 2.0% by weight of the laundry care composition, although higher amounts may be used. Monostearyl phosphate suds suppressors may be utilized in amounts ranging from about 0.1% to about 2% by weight of the laundry care composition. Hydrocarbon suds suppressors may be utilized in amounts ranging from about 0.01% to about 5.0% by weight of the laundry care composition, although higher levels can be used. Alcohol suds suppressors may be used at about 0.2% to about 3% by weight of the laundry care composition.

Suds Boosters

If high sudsing is desired, suds boosters such as the $C_{10}$-$C_{16}$ alkanolamides may be incorporated into the laundry care compositions from about 1% to about 10% by weight of the laundry care composition. Some examples include the C10-C14 monoethanol and diethanol amides. If desired, water-soluble magnesium and/or calcium salts such as $MgCl_2$, $MgSO_4$, $CaCl_2$, $CaSO_4$, and the like, may be added at levels of about 0.1% to about 2% by weight of the laundry care composition, to provide additional suds and to enhance grease removal performance.

Fillers and Carriers

Fillers and carriers may be used in the laundry care compositions described herein. As used herein, the terms "filler" and "carrier" have the same meaning and can be used interchangeably. Liquid laundry care compositions, and other forms of laundry care compositions that include a liquid component (such as liquid-containing unit dose laundry care compositions), may contain water and other solvents as fillers or carriers. Low molecular weight primary or secondary alcohols exemplified by methanol, ethanol, propanol, isopropanol, and phenoxyethanol are suitable. Monohydric alcohols may be used in some examples for solubilizing surfactants, and polyols such as those containing from 2 to about 6 carbon atoms and from 2 to about 6 hydroxy groups (e.g., 1,2-propanediol, 1,3-propanediol, 2,3-butanediol, ethylene glycol, and glycerine may be used). Amine-containing solvents may also be used.

Methods of Use

The present invention includes methods for treating fabric with the laundry care compositions described above. Compact fluid detergent compositions that are suitable for sale to consumers are suited for use in laundry pretreatment applications, laundry cleaning applications, and home care applications. Such methods include, but are not limited to, the steps of contacting detergent compositions in neat form or diluted in wash liquor, with at least a portion of a fabric which may or may not be soiled and then optionally rinsing the fabric. The fabric material may be subjected to a washing step prior to the optional rinsing step. Machine laundry methods may comprise treating soiled laundry with an aqueous wash solution in a washing machine having dissolved or dispensed therein an effective amount of a machine laundry detergent composition in accordance with the invention. An "effective amount" of the detergent composition means from about 20 g to about 300 g of product dissolved or dispersed in a wash solution of volume from about 5 L to about 65 L. The water temperatures may range from about 5° C. to about 100° C. The water to soiled material (e.g., fabric) ratio may be from about 1:1 to about 30:1. The compositions may be employed at concentrations of from about 500 ppm to about 15,000 ppm in solution. In the context of a fabric laundry composition, usage levels may also vary depending not only on the type and severity of the soils and stains, but also on the wash water temperature, the volume of wash water, and the type of washing machine (e.g., top-loading, front-loading, vertical-axis Japanese-type automatic washing machine).

The detergent compositions herein may be used for laundering of fabrics at reduced wash temperatures. These methods of laundering fabric comprise the steps of delivering a laundry detergent composition to water to form a wash liquor and adding a laundering fabric to said wash liquor, wherein the wash liquor has a temperature of from about 0° C. to about 20° C., or from about 0° C. to about 15° C., or from about 0° C. to about 9° C. The fabric may be contacted to the water prior to, or after, or simultaneous with, contacting the laundry detergent composition with water. Another method includes contacting a nonwoven substrate, which is impregnated with the detergent composition, with a soiled material. As used herein, "nonwoven substrate" can comprise any conventionally fashioned nonwoven sheet or web having suitable basis weight, caliper (thickness), absorbency, and strength characteristics. Non-limiting examples of suitable commercially available nonwoven substrates include those marketed under the trade names SONTARA® by DuPont and POLY WEB® by James River Corp.

Hand washing/soak methods, and combined hand washing with semi-automatic washing machines, are also included.

Packaging for the Compositions

The laundry care compositions described herein can be packaged in any suitable container including those constructed from paper, cardboard, plastic materials, and any suitable laminates. An optional packaging type is described in European Application No. 94921505.7.

Multi-Compartment Pouch

The laundry care compositions described herein may also be packaged as a multi-compartment laundry care composition.

Other Adjunct Ingredients

A wide variety of other ingredients may be used in the laundry care compositions described herein, including, for example, other active ingredients, carriers, hydrotropes, processing aids, dyes or pigments, solvents for liquid formulations, solid or other liquid fillers, erythrosine, colliodal silica, waxes, probiotics, surfactin, aminocellulosic polymers, Zinc Ricinoleate, perfume microcapsules, rhamnolipids, sophorolipids, glycopeptides, methyl ester ethoxylates, sulfonated estolides, cleavable surfactants, biopolymers, silicones, modified silicones, aminosilicones, deposition aids, hydrotropes (especially cumene-sulfonate salts, toluene-sulfonate salts, xylene-sulfonate salts, and naphalene salts), PVA particle-encapsulated dyes or perfumes, pearlescent agents, effervescent agents, color change systems, silicone polyurethanes, opacifiers, tablet disintegrants, biomass fillers, fast-dry silicones, glycol distearate, starch perfume encapsulates, emulsified oils including hydrocarbon oils, polyolefins, and fatty esters, bisphenol antioxidants, micro-fibrous cellulose structurants, properfumes, styrene/acrylate polymers, triazines, soaps, superoxide dismutase, benzophenone protease inhibitors, functionalized TiO2, dibutyl phosphate, silica perfume capsules, and other adjunct ingredients, choline oxidase, triarylmethane blue and violet basic dyes, methine blue and violet basic dyes, anthraquinone blue and violet basic dyes, azo dyes basic blue 16, basic blue 65, basic blue 66 basic blue 67, basic blue 71, basic blue 159, basic violet 19, basic violet 35, basic violet 38, basic violet 48, oxazine dyes, basic blue 3, basic blue 75, basic blue 95, basic blue 122, basic blue 124, basic blue 141, Nile blue A and xanthene dye basic violet 10, an alkoxylated triphenylmethane polymeric colorant; an alkoxylated thiopene polymeric colorant; thiazolium dye, mica, titanium dioxide coated mica, bismuth oxychloride, and other actives.

Anti-Oxidant

The laundry care composition may optionally contain an anti-oxidant present in the composition from about 0.001 to about 2% by weight. Preferably, the antioxidant is present at a concentration in the range 0.01 to 0.08% by weight. Mixtures of anti-oxidants may be used.

One class of anti-oxidants used in the present invention is alkylated phenols. Hindered phenolic compounds are a preferred type of alkylated phenols having this formula. A preferred hindered phenolic compound of this type is 3,5-di-tert-butyl-4-hydroxytoluene (BHT).

Furthermore, the anti-oxidant used in the composition may be selected from the group consisting of α-, β-, γ-, δ--tocopherol, ethoxyquin, 2,2,4-trimethyl-1,2-dihydroquinoline, 2,6-di-tert-butyl hydroquinone, tert-butyl hydroxyanisole, lignosulphonic acid and salts thereof, and mixtures thereof.

The laundry care compositions described herein may also contain vitamins and amino acids such as: water soluble vitamins and their derivatives, water soluble amino acids and their salts and/or derivatives, water insoluble amino acids viscosity modifiers, dyes, nonvolatile solvents or diluents (water soluble and insoluble), pearlescent aids, pediculocides, pH adjusting agents, preservatives, skin active agents, sunscreens, UV absorbers, niacinamide, caffeine, and minoxidil.

The laundry care compositions of the present invention may also contain pigment materials such as nitroso, monoazo, disazo, carotenoid, triphenyl methane, triaryl methane, xanthene, quinoline, oxazine, azine, anthraquinone, indigoid, thioindigoid, quinacridone, phthalocianine, botanical, and natural colors, including water soluble components such as those having C.I. Names.

The laundry care compositions of the present invention may also contain antimicrobial agents. Cationic active ingredients may include but are not limited to n-alkyl dimethyl benzyl ammonium chloride, alkyl dimethyl ethyl benzyl ammonium chloride, dialkyl dimethyl quaternary ammonium compounds such as didecyl dimethyl ammonium chloride, N,N-didecyl-Nmethyl-poly(oxyethyl) ammonium propionate, dioctyl didecyl ammonium chloride, also including quaternary species such as benzethonium chloride and quaternary ammonium compounds with inorganic or organic counter ions such as bromine, carbonate or other moieties including dialkyl dimethyl ammonium carbonates, as well as antimicrobial amines such as Chlorhexidine Gluconate, PHMB (Polyhexamethylene biguanide), salt of a biguanide, a substituted biguanide derivative, an organic salt of a quaternary ammonium containing compound or an inorganic salt of a quaternary ammonium containing compound or mixtures thereof.

In one aspect, such method comprises the steps of optionally washing and/or rinsing said surface or fabric, contacting said surface or fabric with any composition disclosed in this specification then optionally washing and/or rinsing said surface or fabric is disclosed, with an optional drying step.

Drying of such surfaces or fabrics may be accomplished by any one of the common means employed either in domestic or industrial settings. The fabric may comprise any fabric capable of being laundered in normal consumer or institutional use conditions, and the invention is suitable for cellulosic substrates and in some aspects also suitable for synthetic textiles such as polyester and nylon and for treatment of mixed fabrics and/or fibers comprising synthetic and cellulosic fabrics and/or fibers. As examples of synthetic fabrics are polyester, nylon, these may be present in mixtures with cellulosic fibers, for example, polycotton fabrics. The solution typically has a pH of from 7 to 11, more usually 8 to 10.5. The compositions are typically employed at concentrations from 500 ppm to 5,000 ppm in solution. The water temperatures typically range from about 5° C. to about 90° C. The water to fabric ratio is typically from about 1:1 to about 30:1.

The following examples further illustrate the subject matter described above but, of course, should not be construed as in any way limiting the scope thereof.

Example 1

This example demonstrates the synthesis of a phenol compound according to the invention.

In a round bottom flask, 15 gram of MPEG 750 (polyethylene glycol capped with a methyl group and having a molecular weight of about 750 dalton), 2.78 gram of (3,5-di-tert-butyl-4-hydroxyphenyl)propionic acid, 2.2 grams of N,N'-dicyclohexylcarbodiimide, 0.3 gram of p-dimethylamino pyridine, and 50 mL methylene chloride were added and stirred at room temperature for 48 hours. After filtering off the white solid, methylene chloride was removed by roto-vap. The product was then re-dissolved into ethyl acetate and washed with water to remove excess MPEG 750.

The resulting compound has the structure of Formula (X) in which $R^1$ and $R^5$ are tert-butyl groups, $R^2$ and $R^4$ are hydrogen, $R^{11}$ is an ethane-1,2-diyl group, $R^{12}$ is —$R^y R^x$, $R^x$ is a methyl group, and $R^y$ is a polymeric substituent of Formula (C) in which $R^{101}$ and $R^{102}$ are each hydrogen.

Example 2

To demonstrate the scorch resistance performance of the phenol compounds of the invention, a series of laboratory foams was made using a standard low density polyether polyurethane foam formulation. A low density, high water level formulation was used in order to match the peak exotherm exhibited by a foam during the production process. Additional heat was also applied by completing the curing process in a microwave. Scorch was evaluated by measuring the yellowness index in the darkest area in the center of the foam. The yellowness index of a control foam made with a commercially stabilized polyol was compared to the yellowness index of foams made with a minimally stabilized polyol spiked with the inventive phenol compounds.

The control foam was made by mixing 100.0 grams of Arcol 3040 ether polyol (Covestro) with 4.53 grams water, 1.0 gram L620 silicone surfactant (Momentive), 12.5 grams Fyrol FR-2 fire retardant (ICL), 0.3 grams Dabco 33LV amine catalyst (Evonik) and 0.3 grams Dabco T-9 stannous octoate (Evonik). After mixing for 30 seconds, 59.8 grams of toluene diisocyante were added and mixed for an additional 8 seconds. The foam mix was then poured into a box and cured in a 160° C. conventional oven for three minutes. Following this oven cure, the foam was immediately placed in a commercial microwave and heated under controlled conditions to achieve a yellowness index of 30-35.

The inventive foams were made using the same formulation with the following change. The Arcol 3040 fully stabilized polyol was replaced with Arcol 16-52 minimally stabilized polyol (Covestro) which had been spiked with a phenol compound according to the invention. In each case, the phenol compound was added at the same molar equivalent. The comparison foam contained 0.64 grams of Irganox 1135 (BASF), a non-reactive hindered phenol. The inventive foams contained respectively 0.72 grams and 0.67 grams of a phenol compound of the invention, which contain an active hydrogen atom capable of reacting with the isocyanate.

Yellowness index measurements indicate the phenol compounds of the invention provided similar or improved scorch resistance compared to non-reactive antioxidants. Further, given the fact that phenol compounds are reacted into the polyurethane foam, it is believed that these phenol compounds will exhibit far less migration than traditional hindered phenol antioxidants.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the subject matter of this application (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the subject matter of the application and does not pose a limitation on the scope of the subject matter unless otherwise claimed. No language in the specification should be construed as indicating any non-claimed element as essential to the practice of the subject matter described herein.

Preferred embodiments of the subject matter of this application are described herein, including the best mode known to the inventors for carrying out the claimed subject matter. Variations of those preferred embodiments may become apparent to those of ordinary skill in the art upon reading the foregoing description. The inventors expect skilled artisans to employ such variations as appropriate, and the inventors intend for the subject matter described herein to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

What is claimed is:

1. A phenol compound comprising a phenyl group, a hydroxy group directly bonded to the phenyl group, two steric hindering groups directly bonded to the phenyl group in positions that are ortho to the hydroxy group, and at least one polymeric substituent bound to the phenyl group, the polymeric substituent comprising three or more monomer units, wherein the polymeric substituent is directly bonded to a linking group, the linking group is directly bonded to a carbon atom of the phenyl group, and the linking group is an oxygen atom, and wherein the polymeric substituent terminates in a hydroxy group.

2. The phenol compound of claim 1, wherein the steric hindering groups are selected from the group consisting of hydroxy groups, alkyl groups, substituted alkyl groups, cycloalkyl groups, substituted cycloalkyl groups, aryl groups, substituted aryl groups, heteroaryl groups, substituted heteroaryl groups, alkoxy groups, substituted alkoxy groups, aryloxy groups, and substituted aryloxy groups.

3. The phenol compound of claim 2, wherein the steric hindering groups are selected from the group consisting of hydroxy groups, alkyl groups, and substituted alkyl groups.

4. The phenol compound of claim 1, wherein each of the monomer units is independently selected from the group consisting of alkyleneoxy groups, oxoalkyleneoxy groups, oxoalkyleneamine groups, alkyleneamine groups, substituted alkylene groups, saccharide groups, halomethylalkyleneoxy groups, and quaternaryammoniummethylalkyleneoxy groups.

5. The phenol compound of claim 4, wherein the monomer units are selected from the group consisting of alkyleneoxy groups and oxoalkyleneoxy groups.

6. The phenol compound of claim 5, wherein the monomer units are selected from the group consisting of ethyleneoxy, propyleneoxy, and butyleneoxy.

7. The phenol compound of claim 1, wherein the hydroxy group and the polymeric substituent are disposed in the para position relative to each other on the phenyl group.

8. A method for producing a polyurethane polymer, the method comprising the steps of:
   (a) providing a polyol;
   (b) providing a polyisocyanate compound;
   (c) providing a phenol compound comprising a phenyl group, a hydroxy group directly bonded to the phenyl group, and at least one polymeric substituent bound to the phenyl group, the polymeric substituent comprising three or more monomer units, wherein the polymeric substituent is directly bonded to a linking group, the linking group is directly bonded to a carbon atom of the phenyl group, and the linking group is an oxygen atom;
   (d) combining the polyol, the polyisocyanate compound, and the phenol compound to produce a reaction mixture; and
   (e) allowing the polyol and the polyisocyanate compound to react to produce a polyurethane polymer.

9. The method of claim 8, wherein the phenol compound further comprises one or more steric hindering groups directly bonded to the phenyl group, wherein the steric hindering group is bonded to the phenyl group in a position that is ortho to the hydroxy group.

10. The method of claim 9, wherein the phenol compound comprises two steric hindering groups directly bonded to the phenyl group.

11. The method of claim 9, wherein the steric hindering groups are selected from the group consisting of hydroxy groups, alkyl groups, substituted alkyl groups, cycloalkyl groups, substituted cycloalkyl groups, aryl groups, substituted aryl groups, heteroaryl groups, substituted heteroaryl groups, alkoxy groups, substituted alkoxy groups, aryloxy groups, and substituted aryloxy groups.

12. The method of claim 11, wherein the steric hindering groups are selected from the group consisting of hydroxy groups, alkyl groups, and substituted alkyl groups.

13. The method of claim 8, wherein each of the monomer units is independently selected from the group consisting of alkyleneoxy groups, oxoalkyleneoxy groups, oxoalkyleneamine groups, alkyleneamine groups, substituted alkylene groups, saccharide groups, halomethylalkyleneoxy groups, and quaternaryammoniummethylalkyleneoxy groups.

14. The method of claim 13, wherein the monomer units are selected from the group consisting of alkyleneoxy groups and oxoalkyleneoxy groups.

15. The method of claim 14, wherein the monomer units are selected from the group consisting of ethyleneoxy, propyleneoxy, and butyleneoxy.

16. The method of claim 8, wherein the polymeric substituent terminates in a hydroxy group.

17. The method of claim 8, wherein the hydroxy group and the linking group are disposed in the para position relative to each other on the phenyl group.

* * * * *